Figure 1:
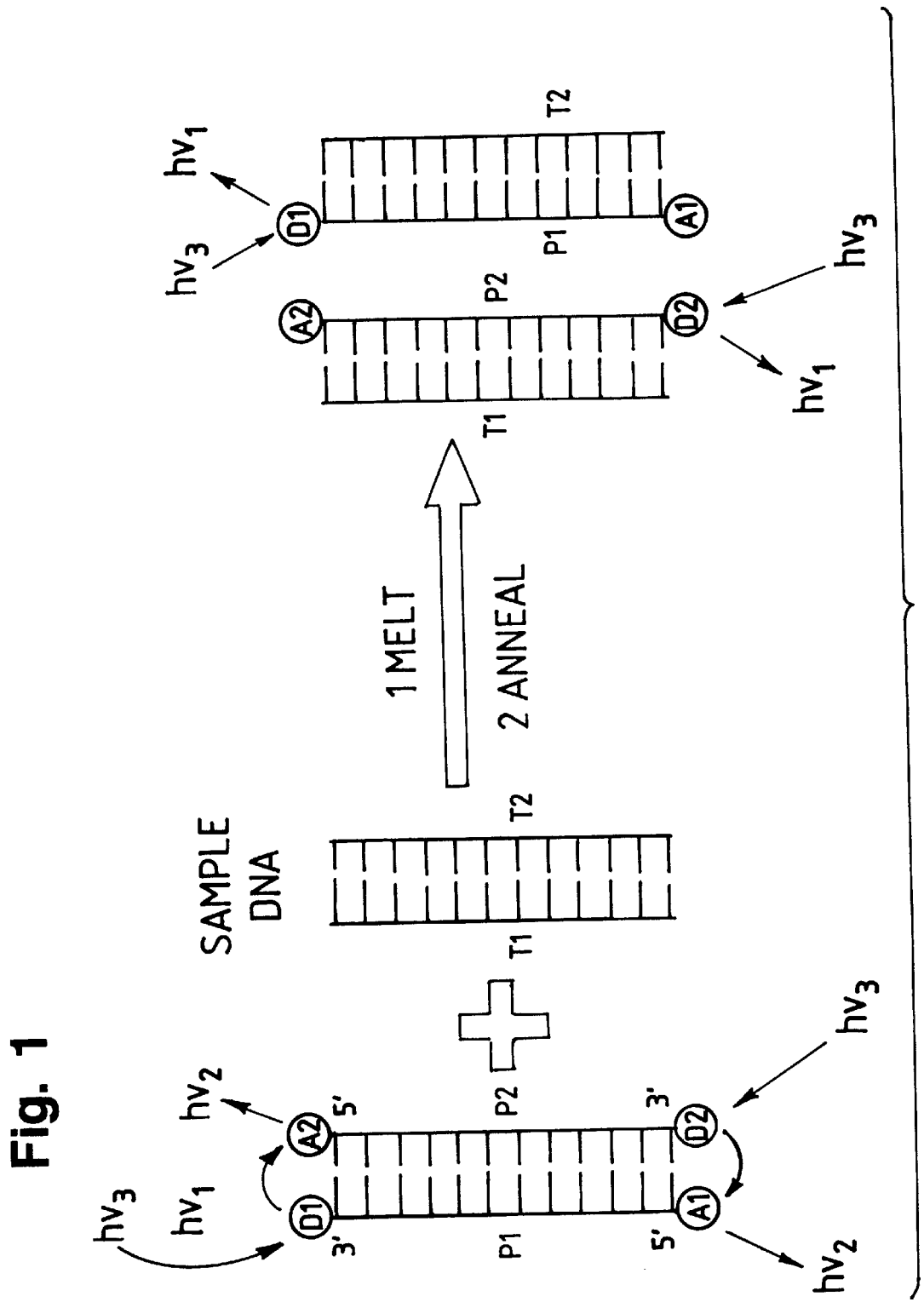

United States Patent [19]
Morrison

[11] Patent Number: 5,928,862
[45] Date of Patent: Jul. 27, 1999

[54] COMPETITIVE HOMOGENEOUS ASSAY

[75] Inventor: Larry E. Morrison, Lisle, Ill.

[73] Assignee: Amoco Corporation, Naperville, Ill.

[21] Appl. No.: 07/559,315

[22] Filed: Jul. 30, 1990

Related U.S. Application Data

[63] Continuation of application No. 06/817,841, Jan. 19, 1986.
[51] Int. Cl.$^6$ ....................................................... C12Q 1/68
[52] U.S. Cl. .............................. 435/6; 436/537; 436/546; 935/78
[58] Field of Search .................................. 435/6; 935/78; 436/537, 546, 800, 805

[56] References Cited

U.S. PATENT DOCUMENTS 4,562,159  12/1985  Shafritz ........................................ 435/6
4,568,649  2/1986  Bertoglio-Matte ....................... 436/537

FOREIGN PATENT DOCUMENTS 0070685  1/1983  European Pat. Off. .
0070687  1/1983  European Pat. Off. .
2139349  11/1984  United Kingdom .

*Primary Examiner*—Christine M. Nucker
*Assistant Examiner*—Laurie Scheiner
*Attorney, Agent, or Firm*—William E. Murray

[57] ABSTRACT

Methods and compositions for performing assays for target polynucleotide strands include contacting a sample with a reagent which includes a first and a second polynucleotide probe. The first and second probes are capable of assuming a first position wherein the probes are bound to each other and a second position wherein the probes are bound to a target. The probes include label moieties capable of interacting to produce a signal indicative of the probes being in one of the two positions.

18 Claims, 12 Drawing Sheets

COMPETITIVE HOMOGENEOUS ASSAY

This is a continuation of application Ser. No. 817,841, filed Jan. 19, 1986.

BACKGROUND OF THE INVENTION

The present invention pertains to methods, reagents, compositions, kits, and instruments for use in the detection and the quantitative analysis of target molecules. In particular, the present invention relates to methods, reagents, compositions, and kits for performing deoxyribonucleic acid (DNA) or ribonucleic acid (RNA) hybridization assays.

The present application is a continuation-in-part of pending applications, U.S. Ser. No. 738,560, filed May 28, 1985, and U.S. Ser. No. 284,469, filed Jul. 21, 1981, which are incorporated by reference herein.

The following definitions are provided to facilitate an understanding of the present invention. The term "biological binding pair" as used in the present application refers to any pair of molecules which exhibit mutual affinity or binding capacity. For the purposes of the present application, the term "ligand" will refer to one molecule of the biological binding pair, and the term "antiligand" or "receptor" will refer to the opposite molecule of the biological binding pair. For example, without limitation, embodiments of the present invention have application in nucleic acid hybridization assays where the biological binding pair includes two complementary strands of polynucleic acid. One of the strands is designated the ligand and the other strand is designated the antiligand. However, the biological binding pair may include antigens and antibodies, drugs and drug receptor sites, and enzymes and enzyme substrates to name a few.

The term "probe" refers to a ligand of known qualities capable of selectively binding to a target ligand. As applied to nucleic acids, the term "probe" refers to a strand of nucleic acid having a base sequence complementary to a target strand.

The term "label" refers to a molecular moiety capable of detection including, by way of example, without limitation, radioactive isotopes; enzymes; luminescent or precipitating agents; and dyes. The term "agent" is used in a broad sense, including any molecular moiety which participates in reactions which lead to a detectable response. The term "cofactor" is used broadly to include any molecular moiety which participates in reactions with the agent.

Genetic information is stored in living cells in thread-like molecules of DNA. In vivo, the DNA molecule is a double helix, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand.

The genetic code of a living organism is carried upon the DNA strand in the sequence of base pairs. DNA consists of covalently linked chains of deoxyribonucleotides and RNA consists of covalently linked chains of ribonucleotides.

Each nucleic acid is linked by a phosphodiester bridge between the 5'-hydroxyl group of the sugar of one nucleotide and the 3'-hydroxyl group of the sugar of an adjacent nucleotide. Each linear strand of naturally occurring DNA or RNA has one terminal end having a free 5'-hydroxyl group and another terminal end having a 3'-hydroxyl group. The terminal ends of polynucleotides are often referred to as being 5'-termini or 3'-termini in reference to the respective free hydroxyl group. Naturally occurring polynucleotides may have a phosphate group at the 5'-terminus. Complementary strands of DNA and RNA form antiparallel complexes in which the 3'-terminal end of one strand is oriented and bound to the 5'-terminal end of the opposing strand.

Nucleic acid hybridization assays are based on the tendency of two nucleic acid strands to pair at their complementary regions. Presently, nucleic acid hybridization assays are primarily used to detect and identify unique DNA or RNA base sequences or specific genes in a complete DNA molecule, in mixtures of nucleic acid, or in mixtures of nucleic acid fragments.

The identification of unique DNA or RNA sequences or specific genes within the total DNA or RNA extracted from tissue or culture samples, may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle anemia, tissue compatibility, cancer and precancerous states, or bacterial or viral infections. The identification of unique DNA or RNA sequences or specific genes within the total DNA or RNA extracted from bacterial cultures may indicate the presence of antibiotic resistance, toxicants, viral or plasmid born conditions, or provide identification between types of bacteria.

Thus, nucleic acid hybridization assays have great potential in the diagnosis and detection of disease. Further potential exists in agriculture and food processing where nucleic acid hybridization assays may be used to detect plant pathogenesis or toxicant producing bacteria.

One of the most widely used polynucleotide hybridization assay procedures is known as the Southern blot filter hybridization method or simply, the Southern procedure (Southern, E., *J. Mol. Biol.*, 98, 503, 1975). The Southern procedure is used to identify target DNA or RNA sequences. The procedure is generally carried out by subjecting sample RNA or DNA isolated from an organism, potentially carrying the target sequence of interest, to restriction endonuclease digestion to form DNA fragments. The sample DNA fragments are then electrophoresed on a gel such as agarose or polyacrylamide to sort the sample fragments by length. Each group of fragments can be tested for the presence of the target sequence. The DNA is denatured inside the gel to enable transfer to nitrocellulose sheets. The gel containing the sample DNA fragments is placed in contact (blotted) with nitrocellulose filter sheets or diazotized paper to which the DNA fragments transfer and become bound or immobilized. The nitrocellulose sheet containing the sample DNA fragments is then heated to approximately 85° C. to immobilize the DNA. The nitrocellulose sheet is then treated with a solution containing a denatured (single-stranded) radio-labeled DNA probe. The radio-labeled probe includes a strand of DNA having a base sequence complementary to the target sequence and having a radioactive moiety which can be detected.

Hybridization between the probe and sample DNA fragments is allowed to take place. During the hybridization process, the immobilized sample DNA is allowed to recombine with the labeled DNA probe and again form double-stranded structures.

The hybridization process is very specific. The labeled probe will not combine with sample DNA if the two DNA entities do not share substantial complementary base pair organization. Hybridization can take from 3 to 48 hours, depending on given conditions.

Unhybridized DNA probe is subsequently washed away. The nitrocellulose sheet is then placed on a sheet of X-ray film and allowed to expose. The X-ray film is developed with the exposed areas of the film identifying DNA fragments which have hybridized to the DNA probe and therefore have the base pair sequence of interest.

The use of nucleic acid hybridization assays has been hampered in part to rather long exposure times to visualize bands on X-ray film. A typical Southern procedure may require one to seven days for exposure. Further, many of the present techniques require radioactive isotopes as labeling agents. The use of radioactive labeling agents requires special laboratory procedures and licenses.

The above problems associated with assays involving radio-isotopic labels have led to the development of immunoassay techniques employing nonisotopic labels such as luminescent molecules. See, generally, Smith et al., *Ann. Clin. Biochem* 18: 253–74 (1981). Luminescent labels emit light upon excitation by an external energy source and may be grouped into categories dependent upon the source of the exciting energy, including: radioluminescent labels deriving energy from high energy particles; chemiluminescent labels which obtain energy from chemical reactions; bioluminescent labels wherein the exciting energy is supplied in a biological system; and photoluminescent or fluorescent labels which are excitable by units of electromagnetic radiation (photons) of infrared, visible, or ultraviolet light. Id. at 255.

Luminescent assay techniques employing labels excitable by nonradioactive energy sources avoid the health hazards and licensing problems encountered with radio isotopic label assay techniques. Additionally, the use of luminescent labels allows for the development of "homogeneous" assay techniques wherein the labeled probe employed exhibits different luminescent characteristics when associated with an assay reagent than when unassociated, obviating the need for separation of the associated and unassociated labeled probe. Nonradioactive nucleic acid type assays, utilizing precipitating, enzymatic, luminescent label moieties, have not conveyed the sensitivity or the specificity to assay procedures necessary to be considered reliable.

In luminescent assays, the presence of proteins and other molecules in biological samples may cause the scattering of the exciting light ("Raleigh scattering") resulting in interference with those luminescent labels which emit light at wavelengths within about 50 nm of the wavelength of the exciting light. The endogenous compounds may also scatter the exciting light at a longer wavelength characteristic of the scattering molecules ("Raman scattering"), or may absorb light in the spectrum of emission of the luminescent label, resulting in a quenching of the luminescent probe.

Attempts to improve the sensitivity of heterogeneous luminescent assays have included the development of so-called "time resolved" assays. See, Soni et al., *Clin. Chem.* 29/1, 65–68 (1983); U.S. Pat. No. 4,176,007. Time resolved assays generally involve employing luminescent labels having emissive lifetimes significantly different from (usually much longer than) the 1–20 nsec emissive lifetime of the natural fluorescence of materials present in the sample. The assay association step is performed and the separated associated or unassociated labeled material is excited by a series of energy pulses provided by a xenon flash tube or other pulsed energy source. Luminescent emission of the label resulting from each pulse is measured at a time greater than the time of the natural fluorescence of background materials in the sample. Interference from the background scattering and short-lived sample fluorescence is thus eliminated from the measured luminescence.

Present techniques which require the separation or immobilization of the probe or sample DNA, heterogeneous assays, may interfere with the operation of nonradioactive assays. Emissions of luminescent label moieties may be quenched by solid supports. Supporting material may be a source of background fluorescence or may reflect or scatter light emissions thereby interfering with the assay. The time required for the step of hybridization is increased when the complementary strands:of DNA are not totally free to orientate due to immobilization of one of the pair of strands in a complementary pairing relationship. Nonspecific binding of the labeled probe to the solid support may decrease the accuracy of the assay.

SUMMARY OF THE INVENTION

It is an object of the present invention to provide methods, reagents, compositions, kits, and instrumentation for performing assays for target polynucleotide strands of interest. Other objects will be presented hereinafter.

Briefly, an embodiment of the present invention includes a method for assaying a sample for target molecules which are members of a biological binding pair. The method includes contacting a sample with reagent under binding conditions wherein the reagent includes a probe member including a probe ligand and a probe antiligand. The probe ligand and probe antiligand are capable of assuming a first bound position to each other and at least one of the probe members is capable of assuming a second bound position to the target molecule. The probe members include a first label moiety positioned on the probe ligand and a second label moiety positioned on the probe antiligand. The first and second label moiety are capable of interacting when the probe ligand and antiligand are in the first bound position to produce a signal capable of detection which is characteristic of the reagent ligand and antiligand in one of the two positions. The sample is monitored for the presence of the signal which is related to the presence of the target molecule.

A further embodiment of the present invention includes a method for assaying a sample for target polynucleotide strands. The method includes contacting a sample with reagent under binding conditions wherein the reagent includes a first polynucleotide probe and a second polynucleotide probe. The first and second probes are capable of assuming a position wherein the probes are bound to each other and at least one of the probes is capable of assuming a second position wherein the probe is bound to the target polynucleotide strand. The first and second probes include a first label moiety positioned on one of the probes and a second label moiety positioned on the opposite probe. The first and second label moieties are capable of interacting when the first and second probes are bound to each other to produce a signal capable of detection characteristic of the reagent strands being in one of the two positions. The sample contacted with the reagent is monitored for the signal, the presence of which is related to the presence of target polynucleotide strands in the sample. The present method allows a polynucleotide sample to be assayed without the need for immobilization steps and without radioactive labeling techniques.

Preferably, at least one label moiety is located at the 3'-terminus of one of the probes and the second label moiety is located at the 5'-terminus of the opposite probe. A plurality of label moieties can be used for each probe, preferably two—one at each termini. For example, a first label moiety may be associated with the first probe at a 3'-position and a second label moiety associated with the 5'-position. A second probe having a similar label moiety organization, a first label moiety in the 3'-position, and a second label moiety in the 5'-position, will hybridize to the first probe such that the first and second label moieties of opposite probes are in close proximity and can interact.

An embodiment of the method of the present invention includes the additional steps of preparing probes by splicing polynucleotide segments having base sequences substantially identical to the target sequences into amplification means to form multiple copies of the reagent polynucleotide segments. Preferably, the amplification means include a high copy number plasmid or phage which, when incorporated into bacteria, is reproduced. The polynucleotide segments having sequences substantially identical to the target sequences are isolated from cellular constituents, and undesirable bacteria, plasmid, or phage DNA, and are subjected to restriction digestion to form segments. The segments are then available for the addition of label moieties to form probes.

Additionally, each plasmid or phage-derived section can be subjected to further restriction enzymes to produce a multitude of subsections to which label moieties can be attached en masse. Each subsection would be capable of hybridizing to a representative portion of the target strand. A multitude of reagent probes from plasmid or phage sources would provide greater signal generating capabilities and would provide probes efficiently and relatively inexpensively.

A further embodiment of the present invention includes methods for nonradioactive labeling of the 3'-terminus of a DNA strand and the resultant compositions. A resultant composition includes a DNA strand having an aminoalkyl derivative of a nucleic acid. The amino group of the nucleic acid can be reacted with amine reactive label moieties. Preferably, the aminoalkyl derivative includes an aliphatic primary amino group. More particularly, a preferred aminoalkyl derivative includes a ribonucleic acid derivative such as an aminohexylaminoadeosine triphosphate which can be attached to the reagent strand by means of the enzyme terminal deoxynucleotidyl transferase (TdT).

Terminal transferase will add one or two ribonucleic acid derivatives to the terminal end of a single-stranded DNA obviating problems inherent in tails of the deoxy-derivative which must be sized to standardize signal strength and which may contribute to steric effects. Labels on tails may no longer possess proper spacial relationship for energy transfer or collisional interaction. However, tails are good if the label moieties on the tails are "silent," e.g., multiple quenchers result in greater quenching activity due to the greater local concentration of quenchers, yet do not result in increased background if the quencher is nonfluorescent.

A further embodiment of the present invention includes a kit for performing assays for target molecules which are part of a biological binding pair. In the case where the target molecule is a segment of nucleic acid having a specific base sequence, the kit includes reagent which includes a first polynucleotide probe and a second polynucleotide probe. The first and second probes are capable of assuming a first position wherein the first and second probes are bound to each other under binding conditions and at least one of the probes is capable of assuming a second position wherein the probe is bound to the target. The first and second probes have at least one label moiety associated with one of the probes and a second label moiety associated with the opposite probe. The first and second label moieties are capable of interacting, when the first and second probes are in the first position, to produce a signal capable of detection which is characteristic of the probes being in one of the two positions.

An embodiment of the present invention further includes an instrument for performing assays in accordance with the present method. In the situation where the target is a polynucleotide segment, the instrument includes a reaction chamber adapted for receiving reagent and target in a substantially mixed homogeneous state. The reagent includes a first polynucleotide probe and a second polynucleotide probe. The first and second probes are capable of assuming a first position wherein the first and second probes are bound to each other under binding conditions and at least one of the probes is capable of assuming a second position wherein at least one of the probes is bound to the target. The first and second probes have at least one label moiety associated with one of the probes and a second label moiety associated with the opposite probe. The first and second label moieties are capable of interacting, when the first and second probes are in the first position, to produce a signal capable of detection which is characteristic of one of the two positions. The instrument further includes suitable detection means for detecting the signal, such as a photomultiplier tube in the case of luminescent agents.

Embodiments of the present instrument adapted for use with fluorescent assays include suitable label excitation means, including lasers or light-emitting assemblies with filters to define appropriate wavelengths or injection apparatus for injecting cofactors in the case of chemiluminescent or enzymatic agents.

A preferred instrument would include time resolved controls to pulse light into the reaction chamber and selectively read fluorescent emissions resulting from energy transfer to reduce background fluorescence.

Turning now to the drawings, which by way of illustration depict preferred embodiments of the present invention, and in particular FIG. 1, a method of procedure, with necessary reagent compositions, is illustrated in schematic form for an assay for a target polynucleotide strand. In conventional assay techniques, more than one target strand and more than one probe strand would be used to perform an assay; however, for simplicity, to further an understanding of the invention, the illustration depicts only a single reagent segment and a single target segment.

FIG. 1 depicts first and second polynucleotide strand probes (P1 and P2, respectively) in a hybridized or mutually-bound first position. Also illustrated is a duplex DNA segment comprised of two complementary target strands of interest (T1 and T2, respectively). The first probe (P1) includes two label moieties, (A1 and D1), at the termini of the strand. A first label moiety (A1) is covalently bonded to the 5'-terminus of the first probe (P1) and a second label moiety (D1) is covalently bonded to the 3'-terminus of the first probe. Similarly, another first label moiety (A2) is covalently bonded to the 5'-terminus of the second probe (P2) and another second label moiety (D2) is covalently bonded to the 3'-terminus of the second probe. The first and second label moieties of opposite probes (A1 and D2) and (A2 and D1) are capable of interacting when the first and second probes are in the first mutually-bound position.

It will be recognized by those skilled in the art that label moieties may be combined or associated with DNA probes in ways other than covalent bonding, for example, without limitation, intercalation, chelation, and ionic, hydrophilic, or hydrophobic affinity. As used herein, the word "associated" encompasses all means of bonding a label moiety to a probe entity.

The label moieties of the present invention are paired or grouped in manners which allow the label moieties to interact. By way of example, without limitation, the label groups may be comprised of combinations of label moieties including a first and second fluorophore, a fluorophore and a chemiluminescent moiety, a chemiluminescent moiety and a cofactor, a precipitating agent and a solubilizing agent, an enzyme and a substrate, and calorimetric moieties and cofactors.

In the present illustration, the first label moieties are fluorophores (A1 and A2) capable of receiving energy or light of a particular wavelength ($hv_1$) and emitting energy or light at second wavelength ($hv_2$). Similarly, the second label moieties are fluorophores (D1 and D2) capable of receiving energy or light of a particular wavelength ($hv_3$) and emitting or transferring energy at a second wavelength ($hv_1$). The first and second fluorophores of opposite probes (A1 and D2) and (A2 and D1) are capable of interacting, when the first and second probes (P1 and P2) are in the first mutually-bound position, such that the light emissions emanating from the second fluorophores is quenched. Further, light of wavelength $hv_3$, not normally capable of being received by the first fluorophores (A1 and A2), results in emissions at wavelength $hv_2$ due to the interaction.

As illustrated in FIG. 1, probes (P1 and P2) are added to or combined with target strands (T1 and T2). The probes and targets are denatured, allowing the strands to separate. Next, the probes and targets are allowed to rehybridize, further allowing the strands to recombine into a second position wherein probes are bound to targets to form probe-target hybrids (PT1 and PT2). The label moieties of each probe strand are removed from label moieties of the opposite probe strand and are unable to interact.

In the first position, wherein the probe strands (P1 and P2) are mutually bound, illumination with light energy of a wavelength ($hv_3$) suitable to excite second fluorophores (D1 and D2) results in the emission of light energy by the first fluorophores (A1 and A2) at a different wavelength ($hv_2$) than the initial excitation wavelength ($hv_3$) or the normal emission wavelength ($hv_1$) of the second fluorophores (D1 and D2). The hybridization of probes (P1 and P2) into a second position with targets (T1 and T2) results in disruption of the interaction between label moieties of opposite probe strands (A1 and D2; and A2 and D1) and a decrease in the emission of light at the emission wavelength ($hv_2$) of first fluorophores (A1 and A2). The decrease in emission of light of the emission wavelength ($hv_2$) of the first label moieties, fluorophores (A1 and A2), is inversely related to the concentration of the target present.

The emissions of second fluorophores (D1 and D2) are normally quenched in the presence of the first fluorophores (A1 and A2) resulting in little or no detectable emission of light energy at the emission wavelength ($hv_1$). However, hybridization of probe strands (P1 and P2) to target strands (T1 and T2) to form probe target hybrids (PT1 and PT2) disrupts the interaction between label moieties of opposite probe strands (A1 and D2; and A2 and D1), allowing a detectable emission of light energy at wavelength ($hv_1$) from the second fluorophores (D1 and D2), which is characteristic and indicative of the probes (P1 and P2) assuming a second position bound to the targets (T1 and T2). The increase in the emission of light at the emission wavelength ($hv_1$) of the second label moieties, fluorophores (D1 and D2), is related to the concentration of the target strand.

The emission values of the first and second label moieties, fluorophores (A1 and A2; and D1 and D2) at the two wavelengths ($hv_1$) and ($hv_2$), can be analytically combined to provide a total value for the concentration of target strand of greater sensitivity and accuracy than either value alone. Either signal can be monitored for the presence of the target strands (T1 and T2).

Due to the choice of first and second fluorophores, light scattering, secondary fluorescence, and limitations in excitation or illumination equipment injecting light onto the fluorophores, it may be difficult to detect multiple signals, and, in particular, the signal of the first fluorophores (A1 and A2) when the probes (P1 and P2) are in a mutually-bound position. Further, the light emission wavelength ($hv_2$) may not necessarily be at the normal emission wavelength of the first fluorophores (A1 and A2) due to the interaction of the second fluorophores (D1 and D2). The light emission ($hv_2$) may be characteristic of the label moieties as a combination or group distinct from the first fluorophores (A1 and A2) or the second fluorophores (D1 and D2) alone, or may be quenched.

After denaturization and reannealing, the label moieties, first and second fluorophores (A and D) of opposite probes may be separated and kept apart by the formation of target and probe duplexes (PT1 and PT2). The formation of target and probe duplexes (PT1 and PT2) destroys the ability of the first Label moiety, fluorophores (A1 and A2) to accept or quench energy from second fluorophores (D1 and D2). The signal generating ability of the second fluorophores (D1 and D2) which donates or sends energy to the first energy accepting fluorophore is generally easier to detect. The increase in magnitude of the signal of the second fluorophores (D1 and D2) is a measure of the concentration and presence of target in a sample. The greater the quantity of target in a particular sample, the greater the intensity of the signal at emission wavelength ($hv_1$) of the second fluorophore produced.

Figure 2:
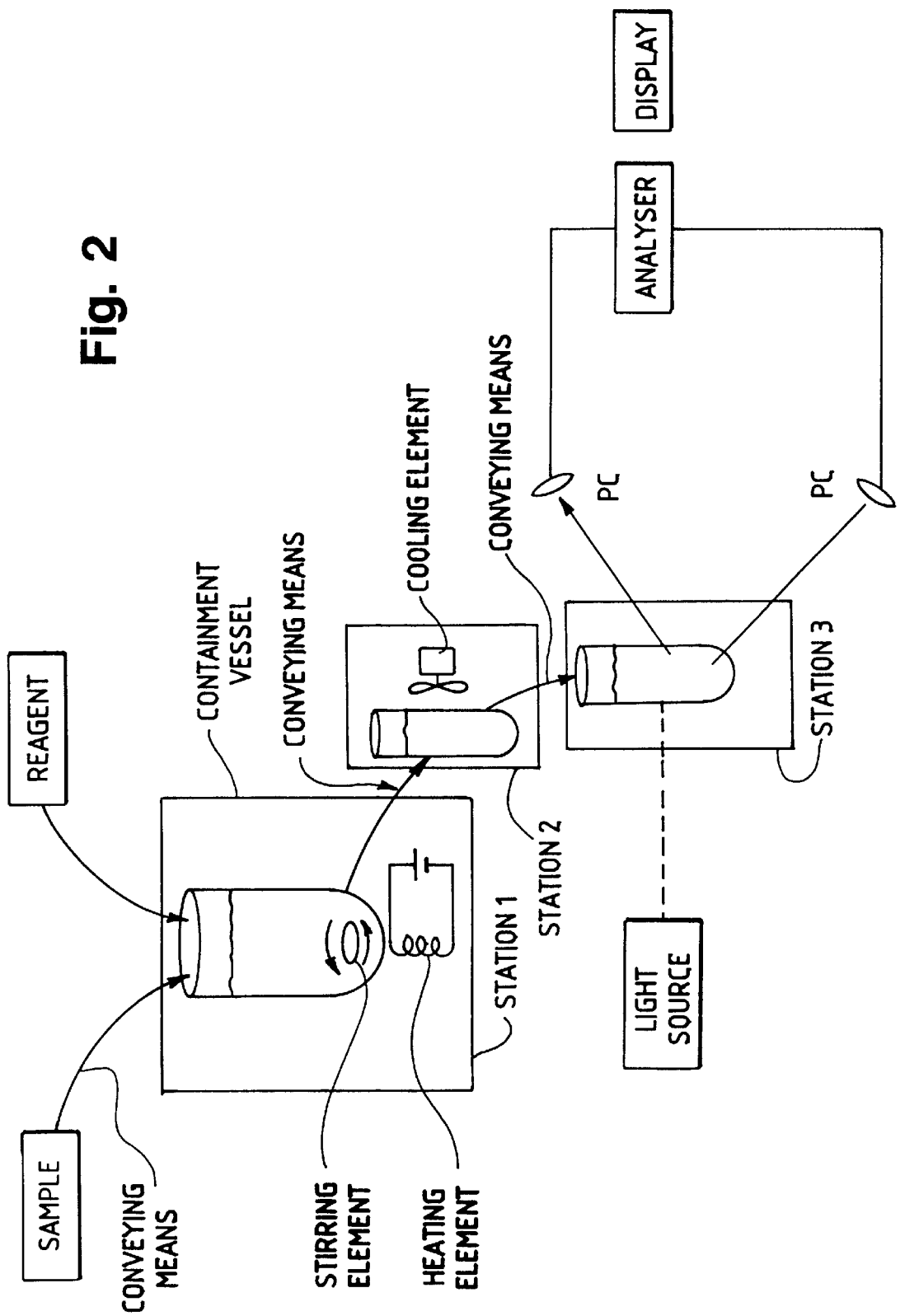

The present method may be practiced with the aid of apparatus set forth in block form in FIG. 2. The apparatus includes the following major elements: an excitation element or light sources a containment vessel, and signal detectors in the form of photon counters (PC).

The containment vessel is adapted for receiving samples, potentially containing target polynucleotide, and reagent. If necessary, the sample is processed to remove all cellular constituents, except for the target polynucleotide, by suitable target capture and release techniques known in the art. Chaotropic salts may be applied to dissolve proteinaceous material in the sample.

The sample is mixed with reagent, including a first probe and a second probe. The first and second probe are capable of assuming a first position wherein the probes are mutually bound to each other and a second position wherein at least one of the probes is capable of binding with the target. Each probe includes first and second label moieties, for example fluorophores, associated with the probe to interact when the probes are in the first mutually bound position. The reagent may also include accelerators known in the art which speed the hybridization process.

In an instrument designed for automated analysis, the apparatus set forth in FIG. 2 would preferably include means for receiving a plurality of containment vessels. Containment vessels containing the sample would be analyzed sequentially. Sample purification, heating, mixing, and reannealing preferably takes place prior to and at a station remote from the station where label signals are measured. Thus, the containment vessels are conveyed from a first station or series of stations where sample purification, heating, and mixing occur, to a second station where probes and target, if present, are allowed to reanneal. The containment vessels are then conveyed to a third station where label signals are monitored.

Conveying means may include a rotatable turntable, conveying belt or other means. As applied in a clinical hospital setting, conveying means may include manual movement. Thus, hospital staff may obtain a tissue sample from a patient and place the sample in the containment vessel. Sample purification, heating, and mixing of reagents would be initiated at bedside and continued as the containment vessel traveled to the third station for monitoring.

Turning now to the first station, a heating element is positioned in close proximity to the containment vessel to heat the sample and probes to melting temperature. Target and probes are able to assume either a first position in which the probes are mutually bound or a second position, if target is present wherein at least one probe is bound to target upon subsequent cooling. The heating element may take many forms including a chemical heat source, electrical heat source, or other means known in the art. The containment vessel includes a stirring or agitation element to facilitate mixing of sample and probes.

From the first station, the containment vessel is conveyed to a second station where probes and target, if present, are allowed to reanneal. To facilitate cooling of the containment vessel from melting or denaturization temperatures, the second station includes a cooling element. The cooling element may not be needed if sufficient time is allowed and surrounding temperatures are cool to permit the probes and target to reanneal.

Leaving the second station, the containment vessel is conveyed to a third station where the signal, characteristic of the probes assuming one of the two positions, is monitored.

The third station includes means to excite one of the label moieties. In the present example, where the first and second label moieties are fluorophores, the excitation means include a light source preferably equipped with suitable filters so as not to cause substantial excitation of the second fluorophore. Alternatively, a laser having an appropriate narrow emission spectrum may be used.

If one of the label moieties included a chemiluminescent agent, the excitation means would include means for injecting into the containment vessel suitable cofactors to produce a light emitting reaction.

The third work station includes signal detectors, photon counters (PC), positioned to receive fluorescent emissions from the containment vessels. Preferably, two photon counters (PC) are used. One photon counter receives signals emanating from the first label moiety and the second photon counter receives signals from the second label moiety through the use of filters or time resolution techniques.

The photon counters produce a photon signal which is received, amplified, and processed by an analyzer. The analyzer processes photon signals into values which can be graphically depicted as illustrated or rendered into other forms which convey the results to an operator.

The present apparatus can be adapted to lifetime resolved techniques with the use of analog defectors in conjunction with a pulsed light source or a sinusoidally modulated light source. A teaching of lifetime resolved techniques is set forth in detail in my copending application, U.S. Ser. No. 738,560, filed May 28, 1985, and incorporated by reference hereto.

The present invention is well suited for use with synthetic oligonucleotides. However, the present invention can be readily adapted to biological cloning techniques to manufacture probes (P1 and P2) in an economical manner.

Figure 3:
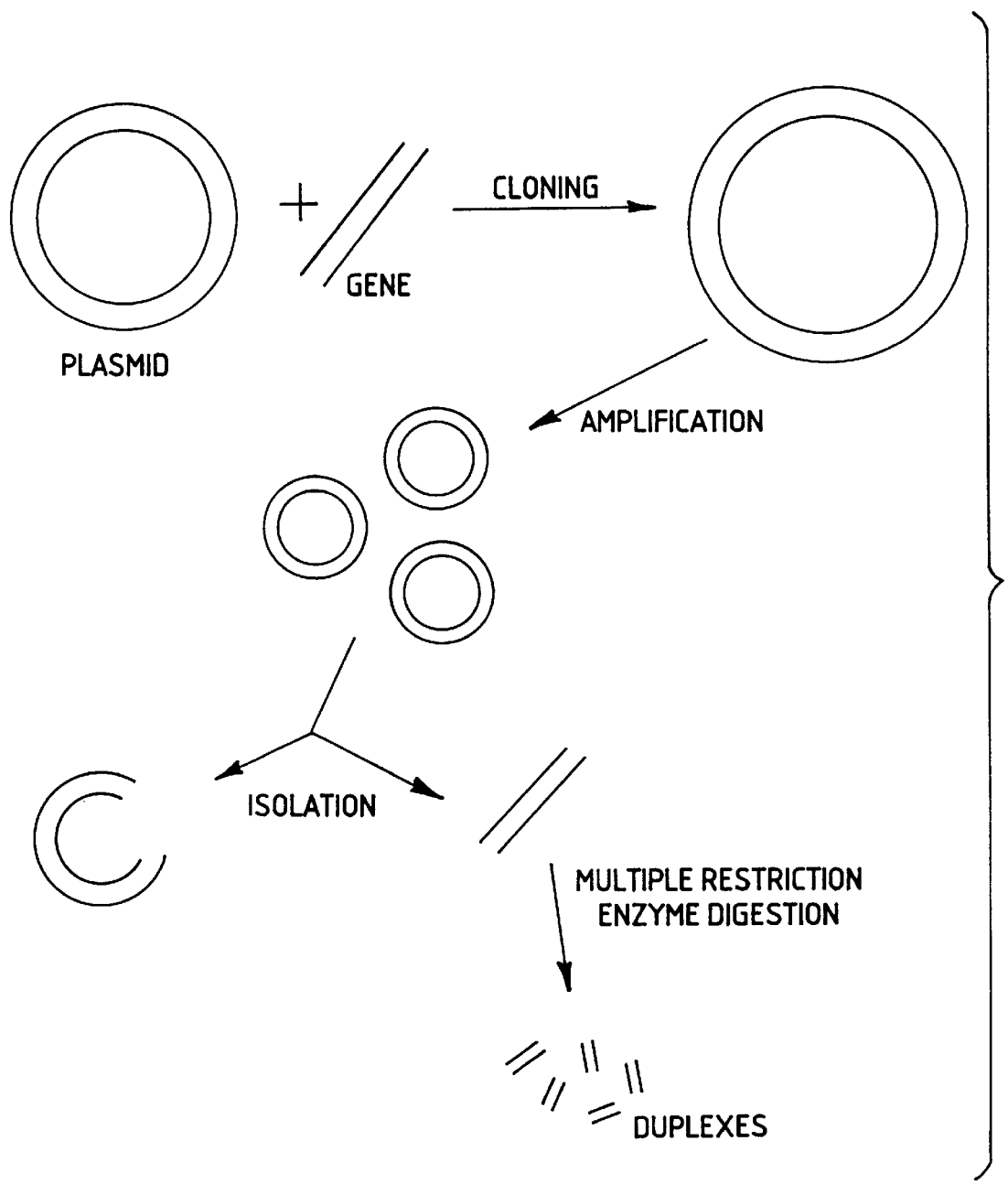

Turning now to FIG. 3, a double-stranded segment (hereinafter referred to as the probe segment) of DNA containing base sequences known to be complementary to target sequence, is introduced into a plasmid by conventional recombinant DNA techniques. For example, the plasmid may be subjected to a restriction endonuclease which cleaves the plasmid ring and provides single-strand protrusions or sticky ends. The sticky ends are complementary and bind to sticky ends at the termini of the probe segment. The probe segment may be incorporated with selection markers to further the identification of successful clones.

The plasmid is then incorporated within a bacterium such as *Escherichia coli* where the plasmid is reproduced or amplified. The bacterium is allowed to grow in colonies on a medium which is toxic to the bacterium except for those successfully incorporating the probe segment and the selection marker.

After the bacteria colonies have been allowed to reproduce and the plasmid allowed to replicate to a high copy number, bacteria and plasmid DNA is isolated from other cellular constituents and the DNA subjected to restriction enzymes to break the probe segment from the plasmid DNA. The probe segments can then be isolated by suitable means, including electrophoresis. The probe segments of interest may be suitable for end labeling to form probes or may consist of parts or subsections which in themselves are valuable as probes. Thus, the larger probe segment may be subjected to multiple restriction enzyme digestion to break up the larger probe segment into smaller probe subsegments suitable for end labeling at the 3'-and 5'-termini.

Labeling at the 3'-termini of the probe segments or subsegments is accomplished with the use of a nucleotide having a functional group available for reacting with an activated fluorophore. The nucleotide having the functional group may be added to the probe segments with the use of terminal deoxynucleotidyl transferase (TdT). The enzyme TdT will only add one or two bases of a ribonucleotide to the probe segments, thus avoiding the addition of a tail or extended chain of the nucleotides to the probe segments. Large tails or chains of the nucleotides may have steric effects that may alter energy transfer between label moieties or alter or impair hybridization of the probe strand to the target strand. Labeling at the 5'-terminus of the probe segments is accomplished by linking a label moiety to the probe segments with the use of a bifunctional aliphatic group. Preferably the label moiety may be linked to the probe segment with an aliphatic diamine.

Turning first to the labeling of a single strand of DNA at the 3'-terminus, the reaction adding a nucleotide to a DNA strand through the use of the enzyme TdT can be written:

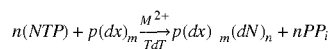

In the above equation, $p(dx)_m$ is an oligodeoxynucleotide of length m bases and N is one of the bases adenine, guanine, cytidine, uridine, thymine, or a modification thereof. The letter n designates the number of monomers that will be added to the DNA strand.

Preferably, the monomer will include an aminoalkyl derivative of a nucleic acid. The amine group can be reacted with a number of fluorescent agents. More preferably, the aminoalkyl derivative includes a primary aliphatic amino group. The use of ribonucleotide monomer in the enzyme TdT limits the addition of monomer bases to the DNA strand, n, to one or two bases. $M^{2+}$ represents a metal ion cofactor. An example of a preferred ribonucleotide derivative includes 8-(6-aminohexyl)-aminoadenosine-5'-triphosphate (AHA-ATP) the structure of which is set forth below:

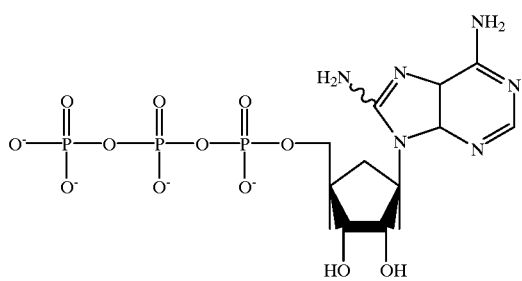

The compound AHA-ATP includes a primary aliphatic amino group which is capable of undergoing a wide variety of chemical reactions permitting the addition of a wide variety of fluorescent labels.

Thus, the 3'-terminus of a strand of DNA will react with AHA-ATP and terminal transferase at pH 7 as set forth below:

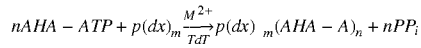

$$nAHA - ATP + p(dx)_m \xrightarrow[TdT]{M^{2+}} p(dx)_m (AHA - A)_n + nPP_i$$

The resultant product strand includes an amino functional group which can be reacted with a label moiety such as precipitating or solubilizing agent, calorimetric agent, luminescent agent, enzyme, or cofactor to produce a probe having a label moiety. By way of example, the fluorophore isothiocyanate reacts with the amine functional group of AHA-A at pH 9.3 to form a probe strand. Other amine-reactive fluorophores include, by way of example, without limitation, fluorescein isothiocyanate, sulforhodamine 101 sulfonic acid chloride (Texas Red), N-hydroxysuccinimidyl pyrenebutanoate, eosin isothiocyanate, and erythrosin isothiocyanate. Suitable chemiluminescent agents and cofactors include amine-reactive luminol derivatives, microperoxidasies, acridinium esters, peroxidases, and derivatives thereof. It will be recognized by those skilled in the art, that fluorescent and chemiluminescent agents not normally amine reactive can be modified to be amine reactive and are suitable as label moieties in the present invention.

The DNA strands may also be labeled at their 3'-termini by tailing the DNA strand with a fluorescent nucleotide derivative such as 1-$N^6$-ethenoadenosine-5'-triphosphate (EATP) mediated through terminal transferase (TdT). However, the application of deoxynucleotides to DNA may produce a tail or chain containing many additions which are difficult to standardize and which may create stearic effects. Other fluorescent nucleotide derivatives include, by way of example, without limitation, 3'-(dimethylaminonaphthoyl)-ATP or-CTP and/or any nucleotide triphosphate incorporating a fluorescent heterocyclic entity.

The 5'-termini of single-stranded DNA can be labeled in a two-step reaction sequence using ethylenediamine to link the strand at the 5'-phosphate to an activated fluorophore as set forth in the reactions below:

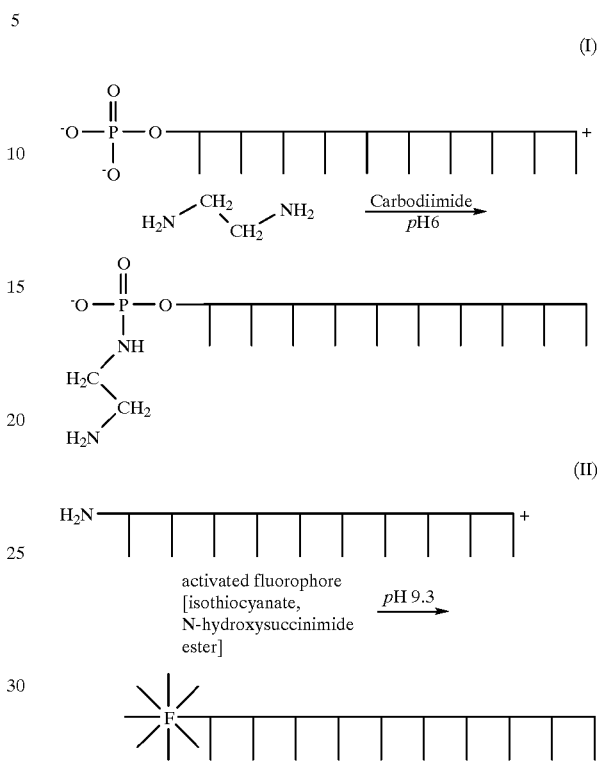

Synthetic polynucleotides will require an additional step to phosphorylate the 5'-hydroxyl group. The phosphorylation can be performed with the enzyme $T_4$ kinase prior to step (I).

Preferably, the carbodiimide is water soluble, including by way of example 1-ethyl-3-(3-dimethylaminopropyl) carbodiimide, 1-cyclohexyl-3-(2-morpholinoethyl) carbodiimide metho-p-toluene-sulfate and derivatives thereof.

The ethylenediamine polynucleotide derivative has a reactive-amine functional group which can be reacted with a label moiety (Step II). The reactive-amine functional group will react with isothiocyanate at pH 9.3 to form a probe strand. Suitable label moieties for one end label, for example 5'-end label, are selected to complement the opposite end label moiety, the 3'-end label. Appropriate fluorophores include, by way of example, without limitation, fluorescein isothiocyanate, sulforhodamine 101 sulfonic acid chloride (Texas Red), N-hydroxysuccinimidyl pyrenebutanoate, eosin isothiocyanate, erythrosin isothiocyanate, and derivatives thereof. Suitable chemiluminescent agents and cofactors include luminol, microperoxidase, glucose oxidase, acridinium esters, lucigenin, and derivatives thereof.

Figure 4:
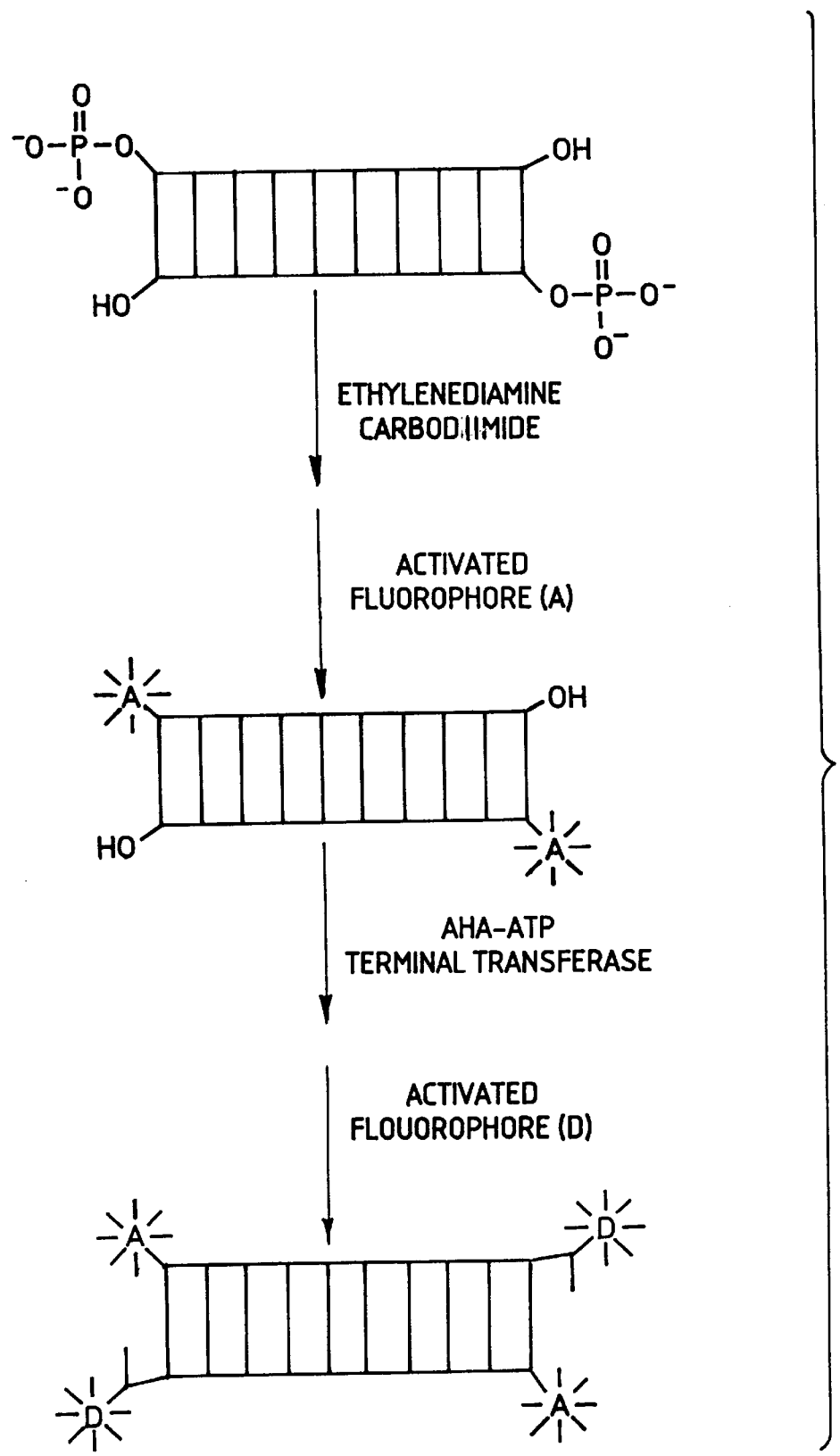

Turning now to FIG. 4, the present labeling techniques as described: in regard to single-stranded DNA are applicable to double-stranded DNA segments isolated from biological sources. Thus, as illustrated, a representative segment of DNA isolated from bacteria plasmids is comprised of two individual complementary strands of DNA each having a 3'-hydroxyl group and a 5'-phosphate group. The double-stranded segment of DNA is reacted with ethylenediamine and an activated fluorophore to covalently affix a first fluorophore (A) to the 5'-phosphate position of both individual strands of DNA concurrently.

Next, the double-stranded segment of DNA is reacted with AHA-ATP, mediated by TdT and reacted with a second fluorophore (D) covalently to the 3'-position of each respective strand. Thus, the first fluorophore (A) of one probe strand is positioned to interact with the second fluorophore of the opposite probe strand at both termini of the DNA segment. The label moieties, first fluorophores (A) and the second fluorophores (D), are able to interact to produce a signal characteristic of one of the two positions the probe may assume upon hybridization with target.

The present invention is further illustrated and described in the following experimental examples which exemplify features of preferred embodiments.

EXAMPLE

A. Materials

In the foregoing examples, 1-$N^6$-ethenoadenosine-5'-triphosphate (sodium), 2'-deoxyadenosine-5'-triphosphate (sodium), DNA oligomers, and oligomers immobilized to cellulose were purchased from Pharmacia Biochemicals, Inc. of Piscataway, N.J. Restriction enzymes were purchased from Bethesda Research Laboratories of Gaithersburg, Md. Terminal deoxynucleotidyl transferase (TdT) of the low molecular weight form was purchased from Life Sciences, Inc. of St. Petersburg, Fla. 8-(6-aminohexyl)-aminoadenosine-5'-triphosphate (AHA-ATP) was purchased from Sigma Chemicals, Inc. of St. Louis, Mo. The plasmid pSP65 was purchased from Promega Biotech of Madison, Wis. Amine-reactive fluorophores were purchased from Molecular Probes, Inc., Junction City, Oreg. All other reagents were of analytical grade or better. Synthetic DNA oligomers were prepared on a Biosearch Sam One automated DNA synthesizer (San Rafael, Calif.) using standard phosphoramadite methods and reagents from several commercial sources, including American BioNuclear of Emeryville, Calif.

In the present example TdT reaction buffer (2X) includes 0.4M cacodylic acid, 0.002M dithiothreitol, 0.016M magnesium chloride at pH 7.1. Binding buffer includes 1M sodium chloride, 0.02M potassium phosphate, monobasic ($KH_2PO_4$) at pH 7.5. Boric acid buffer includes a 0.05M boric acid or 0.05M sodium borate solution adjusted to pH 9.3 with the addition of hydrochloric acid or sodium hydroxide. Absorbance measurements were made to determine DNA probe composition, DNA and DNA probe concentrations, and the degree of base pairing in DNA melting experiments (melting curves). Absorbance spectra were recorded using a Cary 17D abscorbance spectrophotometer (Varian Associates, Palo Alta, Calif.). For measuring absorbance changes of DNA as a function of temperature, the temperature of the thermostated cuvette holder was controlled with a Haake model A81 refrigerated water bath (Saddle Brook, N.J.). Extinction coefficients used in determining homopolymer concentrations were taken from the compilation of extinction coefficients in the appendix of the Pharmacia Molecular Biologicals catalog. The average of the extinction coefficients of homopolymer and alternating homopolymer DNA listed in the same appendix was used to approximate the extinction coefficient for mixed base sequences, $8.7 \times 10^3$ 1/mol/base for single-stranded DNA and $6.8 \times 10^3$ 1/mol/base for double-stranded DNA. Extinction coefficients of unconjugated fluorophores were used to determine the amount of fluorophore present in conjugated DNA probes.

Fluorescence spectra were measured and recorded using an SLM model 4800 analog spectrofluorometer (SLM-AMINCO Instruments, Urbana, Ill.). For greater sensitivity, the analog spectrofluorometer was modified to perform photon counting detection of fluorescence. The modifications included replacing the usual detector, a Hamamatsu model R928 photomultiplier tube in an ambient temperature housing, with the same model photomultiplier tube in a thermoelectric cooled housing (Products for Research model TE-177RF) maintained near −30° C. Current pulses at the anode of the tube were amplified, conditioned, and counted using EG&G ORTEC nuclear instrumentation modules. The modules included a model 9301 fast preamplifier, a model 9302 amplifier-discriminator, and a model 874 quad counter/timer. High voltage for the photomultiplier dynode chain was supplied by an EG&G ORTEC model 478 power supply.

The counter module was interfaced to a Hewlett Packard 9825 computer through an IEEE-488 interface. The computer and interface allowed photon counting spectra to be acquired in coordination with monochromator scanning and reference detector measurements of the unmodified portions of the fluorometer.

Temperature control was maintained with an SLM thermostated cuvette holder in conjunction with a Haake model A81 water bath.

When not scanning, sample emission was generally measured through a second port on the fluorometer which used filters in place of the emission monochromator. For these measurements, the photon counting detector was employed. Emission from samples containing fluorescein labeled DNA was filtered through a Ditric Optics 3 cavity interference filter with peak transmittance centered at 520 nm (FWHM= 8.2 nm). Fluorescein samples were excited at 490 nm with the monochromator bandwidth set at 2 nm. Fluorescence emission as a function of time was recorded using the counter module interfaced to a Hewlett Packard model 9836 computer which allowed data storage and processing of the kinetic information.

A variety of well-known hybridization conditions were employed in the present procedures. A general reference for hybridization conditions may be found in Meinkoth and Wahl, *Analytical Biochemistry*, vol. 138, pp 267–284 (1984).

The following conditions would be applied as necessary by individuals skilled in the art. Optimum rates of hybridization are generally obtained at about 200° to 25° C. below the melting transition temperature. For higher stringency, hybridizations are performed within 5° or 10° C. of the melting temperature. Addition of carrier DNA in the form of lambda DNA was found to improve the stability of probe at low concentration. EDTA was also added, in some instances, to improve DNA stability. Other additives such as concentrators or accelerators could be used in hybridization solutions as long as these were effective for the size oligomers used in preparing the probes and if fluorescence backgrounds were not greatly increased by the addition.

The general procedure employed in experiments herein include a first step—to first render the target and probe DNA in a single-stranded form. This was accomplished by heating the samples containing target and sample DNA in a water bath. For long DNA targets, the samples were generally placed in boiling water baths for approximately 10 minutes in low salt buffers (or distilled water). Probe was added to the sample containing target DNA, often near the end of the dehybridization procedure to avoid prolonged exposure to the high temperature. At the end of the dehybridization, concentrated high salt buffer was added to establish the desired salt and buffer concentration for hybridization. Smaller oligomer targets and probes can be melted in the higher salt hybridization buffer at lower temperature. Usually 1M NaCl was used for hybridizations; however, 100 mM was also used in some instances when it was desired to lower the DNA melting temperature. The single stranded sample containing both target and probe was then allowed to cool to the hybridization temperature and fluorescence measurements performed to ascertain the extent of fluorophore label interaction. The length of the hybridization period varied from minutes, for samples at high probe concentration, to hours for samples containing low concentrations of probe DNA.

The following example sets forth a typical experimental protocol, beginning first with examples which describe 3'-terminal end labeling of probe segments, turning next to 5'-terminal end labeling of probe segments, and finally turning to the application of the end labeled products to a homogeneous competitive assay.

B. 3'-Terminal End Labeling

The 3'-termini of single-stranded DNA were labeled in a two-step reaction. In the first step, the enzyme TdT was used to attach a single nucleotide having a reactive functional group to the 3'-hydroxyl group of each DNA strand. The second step included coupling a label moiety to each DNA strand by a reaction with the reactive functional group.

The following protocol was followed using single-stranded homopolymers of deoxythymidine having base length of twelve ($dT_{12}$) and duplexes of homopolymers of polydeoxyadenosine and polydeoxythymidine, each strand having length of 20 bases ($dA_{20}dT_2$), mixed base synthetic oligomers, and plasmid fragments of pSP65, containing the neomycinphosphotransferase gene fragment, restricted with the enzymes Alu I and Hae III.

Turning now to the first step in more detail, in a standard conical plastic tube about 10 nmole of DNA were combined with 25.5 µl of a 3.3 mM solution of AHA-ATP in water and the sample brought to dryness in a centrifugal vacuum apparatus (Speed Vac, Savant). The ratio of AHA-ATP molecules to 3'-terminal hydroxyl groups of the DNA in the DNA/AHA-ATP solution is approximately 10:1. To the DNA/AHA-ATP solution, 30 µl of TdT reaction buffer, 20 µl bovine serum albumin (500 µg bovine serum albumin per milliliter of water), 500 units of TdT, and water, were added to form 70 µl of a reaction mixture. The reaction mixture was allowed to incubate 18–24 hours in a 37° C. water bath.

Homopolymer individual strands were separated from unreacted AHA-ATP by binding the homopolymer strands to complementary homopolymer immobilized on cellulose particles at 10° C. followed by washing the cellulose at 20° C. with binding buffer. Next, the product was eluted, removed from the cellulose particles, in a 0.05M boric acid buffer at pH 9.3.

Homopolymer duplexes, mixed base oligomers, and pSP65 double-stranded plasmid restriction fragments were separated from the unreacted AHA-ATP by gel permeation chromatography using Sephadex G-25 chromatography media and elution in water or boric acid buffer, or by ion exchange columns such as a NACS ion exchange column manufactured by Bio-Rad Laboratories.

In the second step, referring collectively to single-stranded homopolymers, mixed base oligomers, homopolymer duplexes, or double-stranded plasmid fragments, an amine-reactive fluorophore was covalently bonded to the primary aliphatic amino group of the terminal aminohexyl amino-adenosine formed from the reaction of AHA-ATP with the 3'-terminus of each DNA strand. The amine-reactive fluorophores include sulforhodamine 101 (Texas Red), pyrenebutanoate, fluorescein, eosin and erythrosin, isothiocyanate derivatives, sulfonic acid chlorides, and N-hydroxysuccimide esters. The amine-reactive fluorophores were dissolved in an appropriate nonreactive solubilizing solvent such as acetone for N-hydroxysuccinimidyl pyrenebutanoate, dimethyl formamide for sulforhodamine 101 sulfonic acid chloride, and dimethyl sulfoxide for fluorescein isothiocyanate. A 0.01 molar solution of the fluorophore was added dropwise to a 0.05 molar boric acid/sodium hydroxide buffer solution at pH 9.3 containing the AHA-AMP coupled DNA strands with constant stirring. A 20- to 200-fold molar excess of reactive fluorophore to AHA-AMP coupled DNA was used to force the reaction to the desired products. The reaction was allowed to continue for 16–24 hours. At the end of the reaction period, the fluorophore labeled single-stranded homopolymers were isolated by affinity chromatography. The fluorophore labeled double-stranded homopolymers, mixed base oligomers, and restriction fragments of plasmid pSP65 were isolated on NACS columns or by gel permeation chromatography as outlined above. The fluorophore labeled homopolymer single strands, mixed base oligomers, homopolymer duplexes and double-stranded plasmid fragments were isolated in water or binding buffer. For long-term storage, the fluorophore labeled DNA solutions were reduced to dryness in a centrifugal vacuum concentrator and stored at −20° C.

As an alternative to the two step 3'-labeling technique outlined above, polynucleotides can be labeled directly with fluorescent nucleotidies using the enzyme TdT. By way of further example, single-stranded homopolymer strands were labeled at the 3'-termini with the fluorophore, $1,N^6$-ethenoadenosine triphosphate (EATP), a modified nucleotide, in a procedure identical to the procedure for the addition of AHA-ATP to the 3'-termini of single-stranded DNA.

The above procedures resulted in fluorescent label moieties positioned at the 3'-termini of single- and double-stranded oligomers as identified in Table 1 below.

TABLE 1

3'-Terminal Labeled DNA Oligomers

| Oligomer | Labeling Compound | Labels per Oligomer |
|---|---|---|
| $dT_{12}$ | fluorescein isothiocyanate | 0.88 |
| $dT_{12}$ | fluorescein isothiocyanate | 0.72 |
| $dT_{12}$ | $1,N^6$-ethenoadenosine | 0.95 |
| $dT_{12}$ | $1,N^6$-ethenoadenosine | |
| $dT_{12}$ | sulforhodamine 101 sulfonic acid chloride (Texas Red) | 1.1 |
| $dT_{12}$ | sulforhodamine 101 sulfonic acid chloride (Texas Red) | 0.98 |
| $dT_{12}$ | N-hydroxysuccinimidyl pyrenebutanoate | 0.62 |
| $dT_{12}$ | N-hydroxysuccinimidyl pyrenebutanoate | 0.85 |
| $dT_{12}$ | eosin isothiocyanate | 1.1 |
| $dT_{12}$ | erythrosin isothiocyanate | 2.6 |
| $dT_{20}$ | N-hydroxysuccinimidyl pyrenebutanoate | 0.59 |
| $dT_{20}$ | eosin isothiocyanate | 1.9 |

C. 5'-Terminal End Labeling

The 5'-termini of single-stranded homopolymers of DNA, double-stranded homopolymers of DNA, and restriction fragments of plasmid DNA were labeled in a two-step reaction sequence. In the first step the terminal 5'-phosphate group of the DNA strand was condensed with a reactive difunctional organic molecule capable of linking the 5'-phosphate group to a label moiety, in accordance with B. C. F. Chu, G. M. Wahl, and L. Orgel, *Nucleic Acids Research*, 11(18), 6513–56529 (1983). The second step includes reacting the DNA strand and the reactive organic molecule to the label moiety to form a probe strand.

Those skilled in the art will recognize that many forms of naturally occurring DNA are phosphorylated at the 5'-terminus. Nonphosphorylated DNA requires an initial phosphorylation step using the enzyme $T_4$ kinase, the methods and procedures of which are well-known in the art. See: Bathesda Research Laboratories product profile for 5'-DNA terminus labeling system (incorporated by reference herein).

By way of example, starting with the first step in detail, ethylenediamine was condensed with the terminal 5'-phosphate group of the single-stranded DNA, homopolymer duplexes, and double-stranded restriction fragments of pSP65 plasmid using the water soluble carbodiimide, 1-ethyl-3-(3-dimethylaminopropyl)-carbodiimide. A reaction mixture was formed with 50 nmole of DNA dissolved in 500 µl of water and mixed together with 500 µl of a reactant solution containing 0.5M ethylenediamine, 0.2M carbodiimide, and 0.2M 2-(N-morpholino)-ethane sulfonic acid adjusted to pH 6.0. The reaction mixture was stirred overnight for 16–24 hours at room temperature.

Ethylenediamine reacted single-stranded homopolymers of DNA were purified by adding sodium chloride to the reaction mixture to a one molar concentration and then passing the mixture through a column containing complementary homopolymers immobilized to cellulose at 10° C. The column was then washed with binding buffer at 10° C. and again at 20° C. Ethylenediamine reacted DNA homopolymers were recovered by passing a 0.05M boric acid buffer through the column at temperatures ranging between 50–65° C.

Homopolymer duplexes, mixed base oligomers, and restriction fragments of plasmid DNA were purified by passing the ethylenediamine reacted DNA through a Sephadex G-25 column and eluting with boric acid/sodium hydroxide buffer. An alternative purification method included binding the ethylenediamine reacted DNA to Bio-Rad NACS columns in a low salt buffer and eluting in high salt buffer or 2.0M ammonium acetate. Samples eluded with 2.0M ammonium acetate were dried to remove the salt buffer using either a centrifugal vacuum apparatus or a lyophylizer.

In the second step, the DNA strand bonded to the reactive organic moiety, ethylenediamine, was reacted further with a reactive fluorophore to form a probe strand. In more detail, amine-reactive fluorophores, either isothiocyanate derivatives or N-hydroxysuccimide esters were dissolved in an appropriate nonreactive solubilizing solvent. A 0.01M fluorophore solution was added dropwise to a 0.05M boric acid buffer solution containing the ethylenediamine reacted DNA at pH 9.3 with constant stirring. The reactive fluorophore was added in a 20- to 200-fold molar excess to force the reaction to the desired products. The reaction was allowed to continue for 16–24 hours with stirring.

At the end of the reaction period, the 5'-fluorophore labeled DNA was filtered. The 5'-fluorophore labeled homopolymer single-stranded DNA was isolated by affinity chromatography. The 5'-fluorophore labeled duplex DNA, mixed base oligomers, or labeled plasmid restriction fragments were isolated on NACS columns or by gel permeation chromatography. The 5'-fluorophore labeled duplex homopolymers or plasmid restriction fragments were then isolated in water or binding buffer. The 5'-fluorophore labeled single-stranded DNA are identified in Table 2 set forth below:

TABLE 2

5'-Terminal Labeled DNA Oligomers

| Oligomer | Labeling Compound | Labels per Oligomer |
|---|---|---|
| $dA_{12}$ | fluorescein isothiocyanate | 0.89 |
| $dA_{12}$ | fluorescein isothiocyanate | 0.96 |
| $dA_{12}$ | N-hydroxysuccinimidyl pyrenebutanoate | 0.70 |
| $dA_{20}$ | fluorescein isothiocyanate | 1.1 |
| $d(AC)_5$ | fluorescein isothiocyanate | 0.59 |
| $d(AC)_5$ | fluorescein isothiocyanate | 0.90 |

The 5'-terminal labeled homopolymer probe strands are capable of binding to complementary 3'-terminal homopolymer strands to form a duplex in which the 3'-label moiety of one strand is in a position to interact with the 5'-label moiety of the opposite strand. The 5'- and 3'-homopolymer duplex strands and plasmid restriction fragments include two end labeled complementary polynucleotide strand probes.

Multiple duplex probes were also prepared from synthetic DNA for *E. Coli* enterotoxin gene. Complementary pairs of oligomers were synthesized and then labeled. Five pairs of oligomers were prepared with sequences corresponding to 5 different regions on the genome of an *E. Coli* enterotoxin gene. Four pairs contained oligomers which were 21 bases long and one pair contained oligomers which were 22 bases in length. The 10 single-stranded oligomers were divided into two groups for labeling. One group contained one member of each complementary pair and the other group contained the other pair members. Non-complementary strands were grouped to avoid hybridized DNA in the terminal transferase reaction mixture. The enzyme addition of terminal nucleotide is less efficient when using a blunt end double stranded DNA primer. Labeling efficiency in this preparation was not as high as was obtained in previous duplex probe preparations although the fluorescence change associated with hybridization was large enough that it could be detected at fairly low probe concentrations.

The homopolymer duplexes, plasmid restriction fragments, and toxin gene probes are identified in Table 3 set forth on a following page.

TABLE 3

Dual Terminal Labeled Duplexes

| Duplex | 5'- Labeling | | 3'- Labeling | | Fluorescein Intensity Unhybridized Over Hybridized Form |
|---|---|---|---|---|---|
| | Labeling Compound | Labels per Duplex | Labeling Compound | Labels per Duplex | |
| $dA_{20}\cdot dT_{20}$ | fluorescein isothiocyanate | 0.61 | N-hydroxysuccimidyl pyrenebutanoate | 1.0 | 3.9 |
| $dA_{20}\cdot dT_{20}$ | fluorescein isothiocyanate | 1.2 | eosin isothiocyanate | 3.1 | 2.6 |
| *Plasmid I | fluorescein isothiocyanate | 3.2 | N-hydroxysuccinimidyl pyrenebutanoate | 2.7 | 4.1 |
| *Plasmid II | fluorescein isothiocyanate | 1.3 | N-hydroxysuccinimidyl pyrenebutanoate | 1.4 | 4.0 |
| *Plasmid III | N-hydroxysuccinimidyl pyrenebutanoate | 1.7 | fluorescein isothiocyanate | 0.32 | 0.91 |
| **Toxin | fluorescein isothiocyanate | (+)0.45 (−)0.49 | N-hydroxysuccinimidyl pyrenebutanoate | (+)0.46 (−)0.60 | 2.3 |

*pSP65 (Promega Biotec, Madison, WI) containing neomyocin phosphotransferase gene, restricted with Alu I and Hae III enzymes.
**Synthetic oligomers complementary to *Escherichia Coli* enterotoxin gene.

Referring now to Table 3, the homopolymer duplexes, mixed base oligomers, and plasmid restriction fragments incorporate labels at both the 3'-termini and the 5'-termini of each individual strand. Tables 1, 2, and 3 include an indication of labels per duplex or labels per strand as an indication of the efficiency of the labeling reactions. The number of labels per probe was determined by absorbance spectroscopy.

Figure 5:
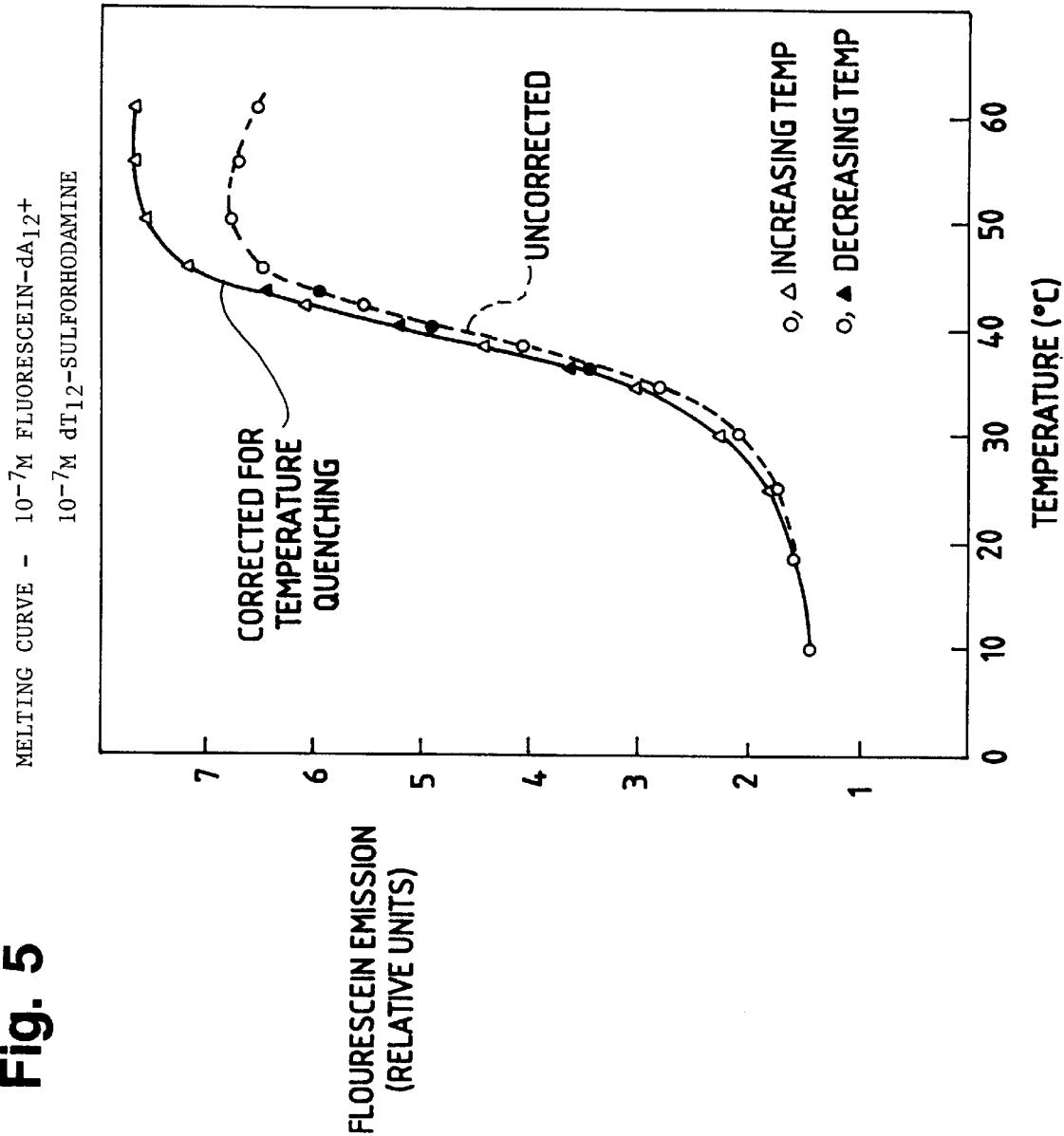

The label moieties of complementary probe strands are capable of interacting when the probe strands are in a mutual, bound position as graphically illustrated in FIG. 5. FIG. 5 sets forth a relationship between fluorescein emission versus temperature as the temperature is varied over the melting point of the hybridized probes. The probes include a homopolymer duplex of deoxyadenosine and deoxythymidine of 12 base length bearing label groups of a 5'-fluorescein and 3'-sulforhodamine, respectively. As illustrated, solid circles and triangles represent values obtained as the temperature of a sample containing probes was decreasing. Open figures of triangles and circles represent values obtained as the temperature of a sample containing probe was increasing. Points represented by triangles reflect values corrected for temperature quenching of the fluorescent moieties. The points represented by circles represent actual values.

In more detail, the melting curve data of FIG. 5 was recorded on samples of DNA in buffer consisting of 1N NaCl and 0.02N potassium phosphate at pH 7.5. Data plotted in FIG. 5 were obtained by mixing equimolar amounts (0.1 $\mu$M) of 5'-fluorescein-$dA_{12}$ and $dT_{12}$-sulforhodamine-3' and measuring the fluorescein emission after sample equilibration at a number of sample temperatures. Fluorescence of 5'-fluorescein-$dA_{12}$ alone was also measured at the same temperatures to determine the effect of temperature on the fluorescein emission. The data from the 5'-fluorescein-$dA_{12}$ alone measurements were used to correct the melting curve recorded on the two-probe sample. Both corrected and uncorrected data are plotted.

As the probes are cooled and reannealed, fluorescein emissions are quenched resulting in a decrease in the fluorescein signal intensity. As the probes are heated to melting or denaturing temperature, the probes separate disrupting the interaction between the label moieties. Fluorescein emissions are no longer quenched and fluorescein emissions increase.

Figure 6:
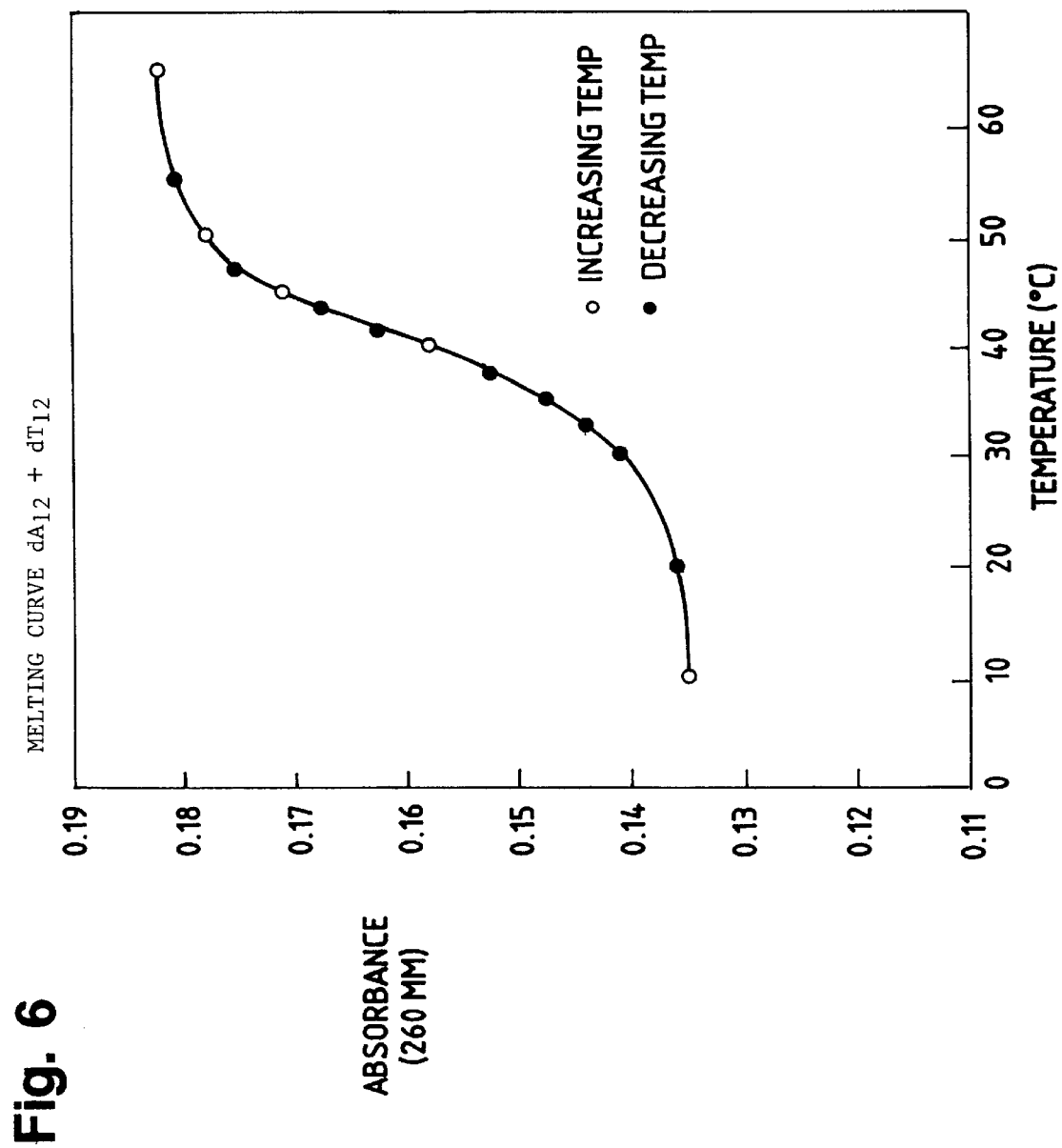

The interaction of the label moieties, set forth in FIG. 5, corresponds to melting temperature data of "unlabeled" probes, as measured by conventional procedures for measuring DNA hybridization in solution. FIG. 6 sets forth graphically the relationship between absorbance of light energy at 260 nM and temperature as the temperature is varied through the melting temperature of unlabeled probes. The probe represented in FIG. 6 includes homopolymers of deoxyadenosine and deoxythymidine of twelve base length. Points on the graph represented by solid circles represent readings as the temperature of the sample was decreasing. Open circles represent readings as the temperature of the sample was increasing. As the temperature of the probes is varied through the melting temperature of the probes, the absorbance at 260 nM increased from approximately 0.135 to 0.182 due to the reduction in base pairing. The melting temperature of the unlabeled DNA as determined by absorbance measurements is identical to the melting temperature determined by fluorophore interaction, indicating that labeling of the DNA does not interfere with the hybridization process.

The interaction of label moieties is also represented in Tables 3 and 4. Table 3 includes a comparison of fluorescein intensity of labeled hybridized homopolymer complexes and plasmid restriction fragments to unhybridized forms. The ratio of the signal of unhybridized probes to the signal of hybridized probe can be as high as 4.1.

Table 4, a comparison of fluorescence intensity of unhybridized labeled probes over hybridized labeled probes, is set forth on the following page:

TABLE 4

Fluorophore Interaction in Complementary Single Labeled Probes

| 5' Labeled Oligo-dA | 3' Labeled Oligo-dT | Oligomer Length (Bases) | Label Detected | Fluorescence Intensity- Unhybridized Over Hybridized Form |
|---|---|---|---|---|
| fluorescein | sulforhodamine 101 | 12 | 5' | 5.4, 1.7 |
| fluorescein | pyrenebutanoate | 12 | 5' | 6.2, 6.9, 6.0 |
| pyrenebutanoate | fluorescein | 12 | 3' | 1.4 |
| pyrenebutanoate | pyrenebutanoate | 12 | both | 1.5 |
| fluorescein | fluorescein | 12 | both | 1.7 |
| acridine | fluorescein | 12 | 3' | 1.2 |
| acridine | sulforhodamine 101 | 12 | 3' | .88 |
| fluorescein | ethenoadenosine | 12 | 5' | 0.67 |
| fluorescein | eosin | 12 | 5' | 2.8, 13.5 |
| fluorescein | erythrosin | 12 | 5' | 1.8 |
| fluorescein | eosin | 20 | 5' | 5.9 |
| fluorescein | pyrenebutanoate | 20 | 5' | 3.6 |

In Tables 3 and 4, the fluorescence changes are, reported as the ratio of the fluorescence of one or both labels in the unhybridized state to the fluorescence observed under hybridization conditions. The data was acquired either from experiments where temperature was used to select the hybridization state, from experiments where complementary probes were examined together and then alone, or from experiments where hybridization of probes was conducted in the presence or absence of a large excess (usually tenfold or greater) of unmodified complementary DNA. In the latter experiments, the large excess of target DNA provides for a competitive hybridization reaction that prevents complementary DNA probes from hybridizing to one another. Multiple values of fluorescence changes are entered for probe pairs for which different preparations of the same labeled oligomers were examined. Table 4 contains data obtained using probes which were prepared by single labeling of oligomers. The compositions of these probes are listed in Tables 1 and 2. The data of Table 3 is derived from probes which were labeled while paired such that a first fluorophore is carried on the 5'-termini of each oligomer and a second fluorophore is carried on the 3'-termini. In the hybridizing condition, the 5' first fluorophore of one strand is in close proximity to the 3' second fluorophore of the complementary strand.

Tables 3 and 4 reveal several label combinations which give rise to significant alterations in the fluorescence of at least one of the two labels. In a Forster energy transfer type mechanism, the label which absorbs and emits light of longer wavelength is expected to receive energy from the other label (energy donor) upon excitation of that label. This results in a quenching of emission from the energy donor label accompanied by an increase in emission from the energy receiving label, if that label is fluorescent. Label combinations which show behavior compatible with this mechanism are fluorescein/sulforhodamine 101, acridine/sulforhodamine 101, fluorescein/ethenoadenosine, fluorescein/eosin, and fluorescein/erythrosin.

However, Tables 3 and 4 reveal several interactions which do not behave in accordance with a Forster type mechanism. Label combinations showing behavior inconsistent with a Forster type energy transfer mechanism are fluorescein/pyrenbutanoate and fluorescein/acridine.

Even though several label combinations exhibit behavior typical of Forster type energy transfer, the mechanism of the interaction cannot be confirmed by data collected from only one of the two Labels. In the label combinations examined, the other member of the label pair was either essentially nonfluorescent when attached to DNA (e.g., acridine) or displayed fluorescence which was fairly insensitive to the state of hybridization. The uncertainty in the mode of label interaction is a result of the ability to bring two label molecules to within a collisional distance of one another. When collisional interactions are allowed the various mechanisms of dynamic quenching may compete and dominate the observed interactions. Close-range dynamic interactions are also potentially more striking in effect than the static counterparts.

Some fluorescence changes noted in Tables 3 and 4 are larger than those observed in quenching and energy transfer-based immunoassays which must rely upon random labeling of protein molecules (i.e., antibodies and/or protein antigens) to prepare one or both of the labeled species. Only a small fraction of labels, therefore, might lie in the proper position for static or collisional interaction with one another in an antibody:antigen complex. Selective labeling of DNA termini, on the other hand, permits the accurate positioning of opposing labels such that collisional interactions are allowed, or static interactions intensified, by all labels in hybridized probe strands.

The data in Tables 3 and 4 also point out the necessity to properly choose the manner in which labels are attached to DNA. In the example where fluorescein is placed on the 3'-terminus and pyrenebutanoate is placed on the 5'-terminus, little if any label interaction is observed while considerable interaction is detected where fluorescein is placed on the 5'-terminus and pyrene is placed on the 3'-terminus. This was observed with homopolymer oligomers as well as restriction enzyme digested plasmid DNA. The difference in label placement relates to the different chemistries used in attaching DNA to the two different termini, the 3'-label being attached via an aminohexylaminoadenosine linker arm while the 5'-label was attached via an ethylenediamine linker.

D. Competitive Assays

The reagent probes of the present invention were applied to competitive DNA assays. The present hybridization procedure is typical for probes including 5'-fluorescein-$dA_{12}$ and $dT_{12}$-sulforhodamine-3' homopolymers.

Figure 7:
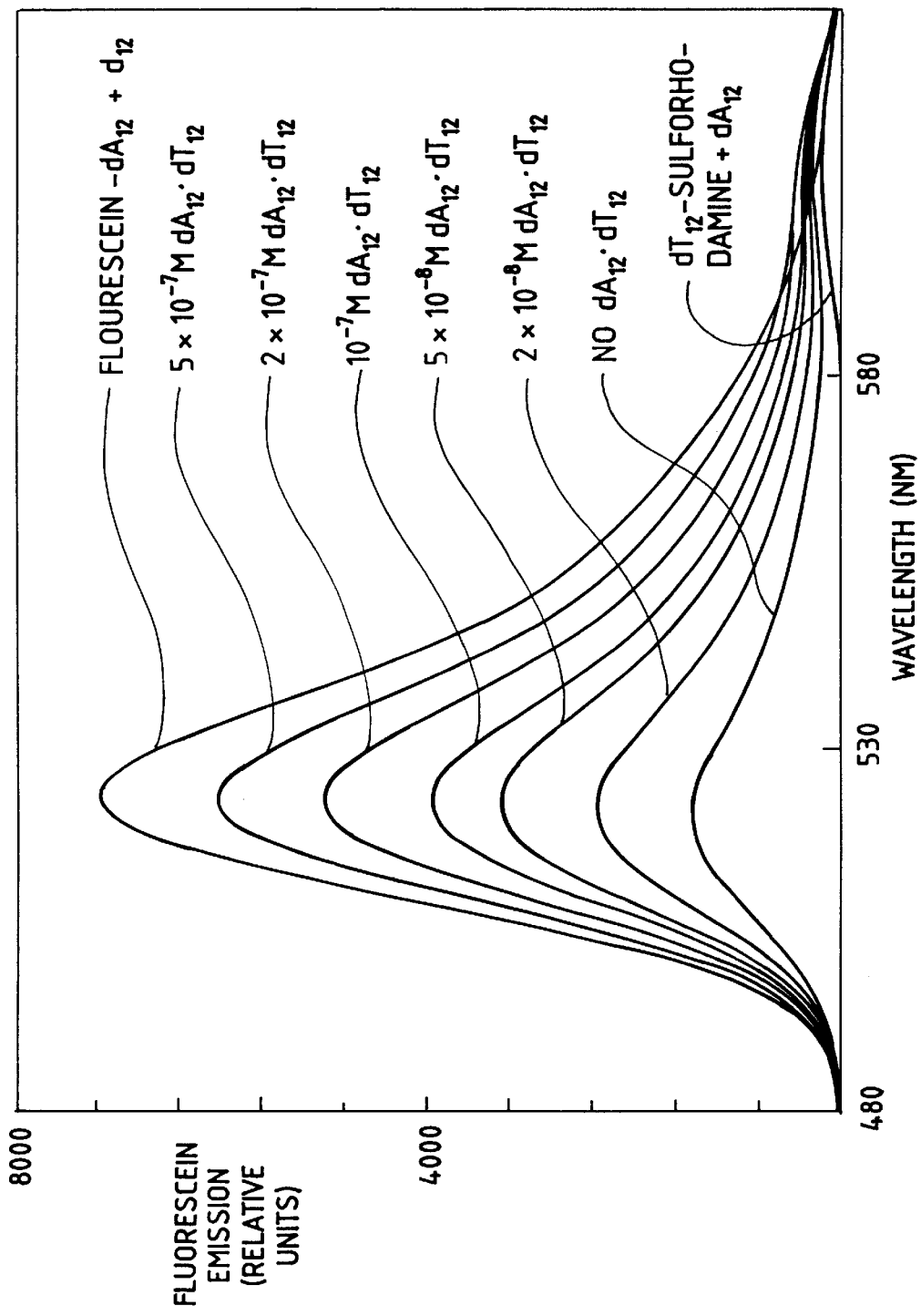

Reference is made to FIG. 7, in which solutions of probes and target DNA were mixed. The probe concentration was fixed at 0.1 $\mu$M and target concentration varied between none to 0.5 $\mu$M. Probes were mixed with target DNA, sufficient water, and a buffer to provide final concentrations of 1.0M sodium chloride and 0.01–0.02M potassium phosphate (monobasic) at pH 7.5 to form a hybridization solution. The solutions were heated to 65° C. for 15 minutes in a water bath to insure complete dehybridization of target and probe DNA. The samples were next cooled to 10° C. for two hours to allow competitive hybridization to occur.

FIG. 7 illustrates the relationship in graphical form of fluorescent intensity in relative units versus wavelengths for various concentrations of target strands with a fixed concentration of $10^{-7}$ molar probe duplex consisting of fluorescein isothiocyanate (fluorescein) labeled deoxyadenosine homopolymer and sulforhodamine sulfonic acid chloride (sulforhodamine) labeled deoxythymidine homopolymer of 12 base length. All samples were illuminated with light energy of 300 nm.

The peak fluoresent activity, at the approximate wavelength of 520 nm, varies with the change in concentration of target homopolymers of deoxyadenosine and deoxythymidine of twelve base length.

Figure 8:
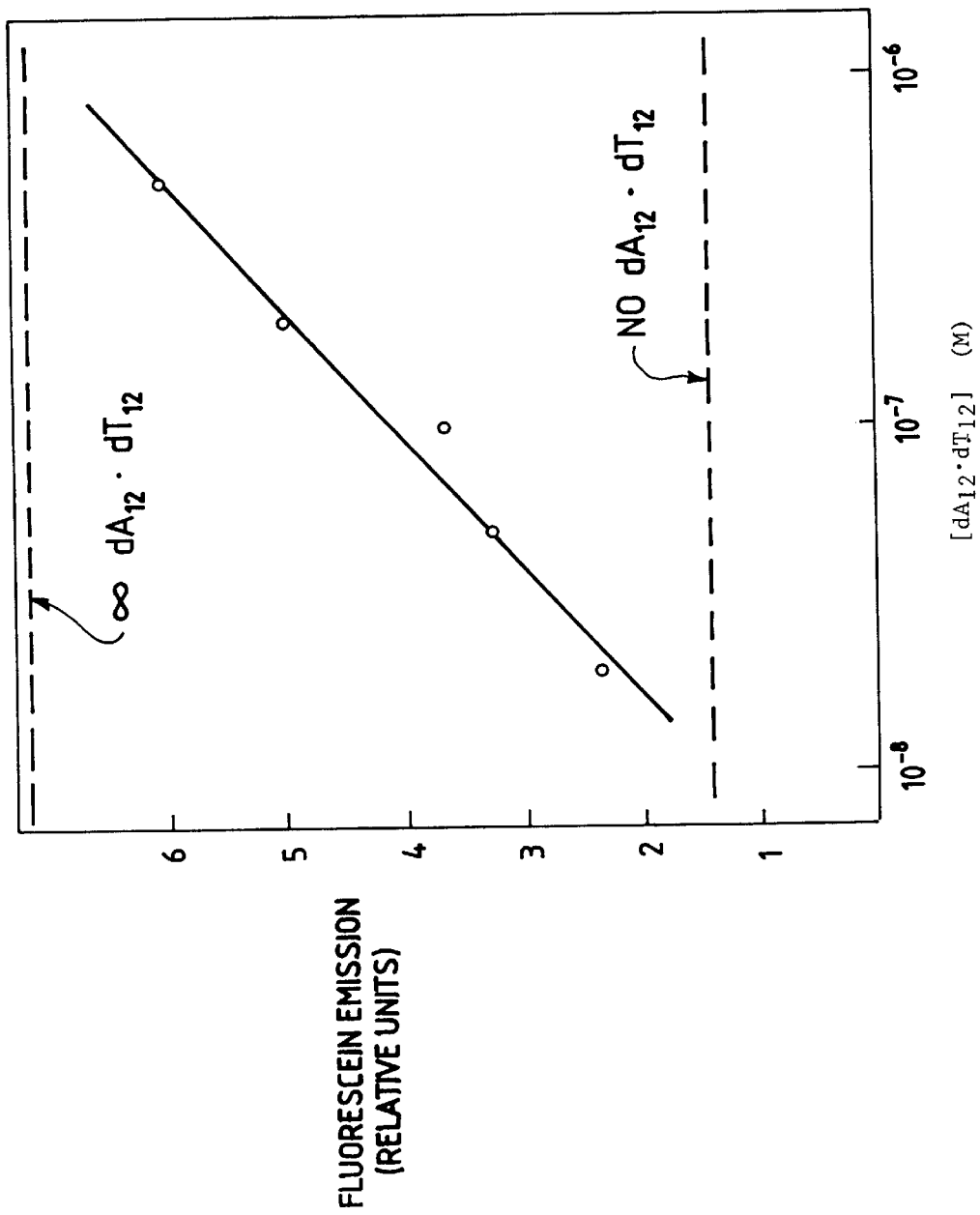

FIG. 8 describes the relationship of fluorescein emissions to the concentration of target. The points of the graph of FIG. 8 are the peak values of the graph of FIG. 7, using fixed concentration of probe. As target concentration increases, the amount of fluorescein quenching by sulforhodamine decreases and fluorescein emissions increase.

The hybridization data presented previously for the 5'-fluorescein-dA$_{12}$/dT$_{12}$-pyrenebutanoate3' system served to demonstrate the concept of a competitive DNA hybridization assay based upon interacting labels. To be a useful assay system, however, the technique must be shown to be specific and sensitive.

The data in FIGS. 9 through 12 serve to demonstrate these aspects of the label interaction assay. Label specificity is demonstrated in FIG. 9 using a duplex probe, the first dA$_{20}$:dT$_{20}$ derived probe listed in Table 3.

In this experiment, 50 nM solutions of probe were mixed with various concentrations of three different target DNAs in water. One target consisted of equimolar amounts of dA$_{20}$ and dT$_{20}$, the appropriate target for hybridization with the probe. The two noncomplementary targets were calf thymus DNA and lambda phage DNA. The samples were heated for six minutes in a boiling water bath and allowed to cool to room temperature. The samples were then diluted in half with 2× concentrated binding buffer to give final NaCl and potassium phosphate concentrations of 100 mM and 10 mM, respectively, at pH 7.5. Room temperature fluorescence spectra were recorded for each sample shortly thereafter.

Figure 9:
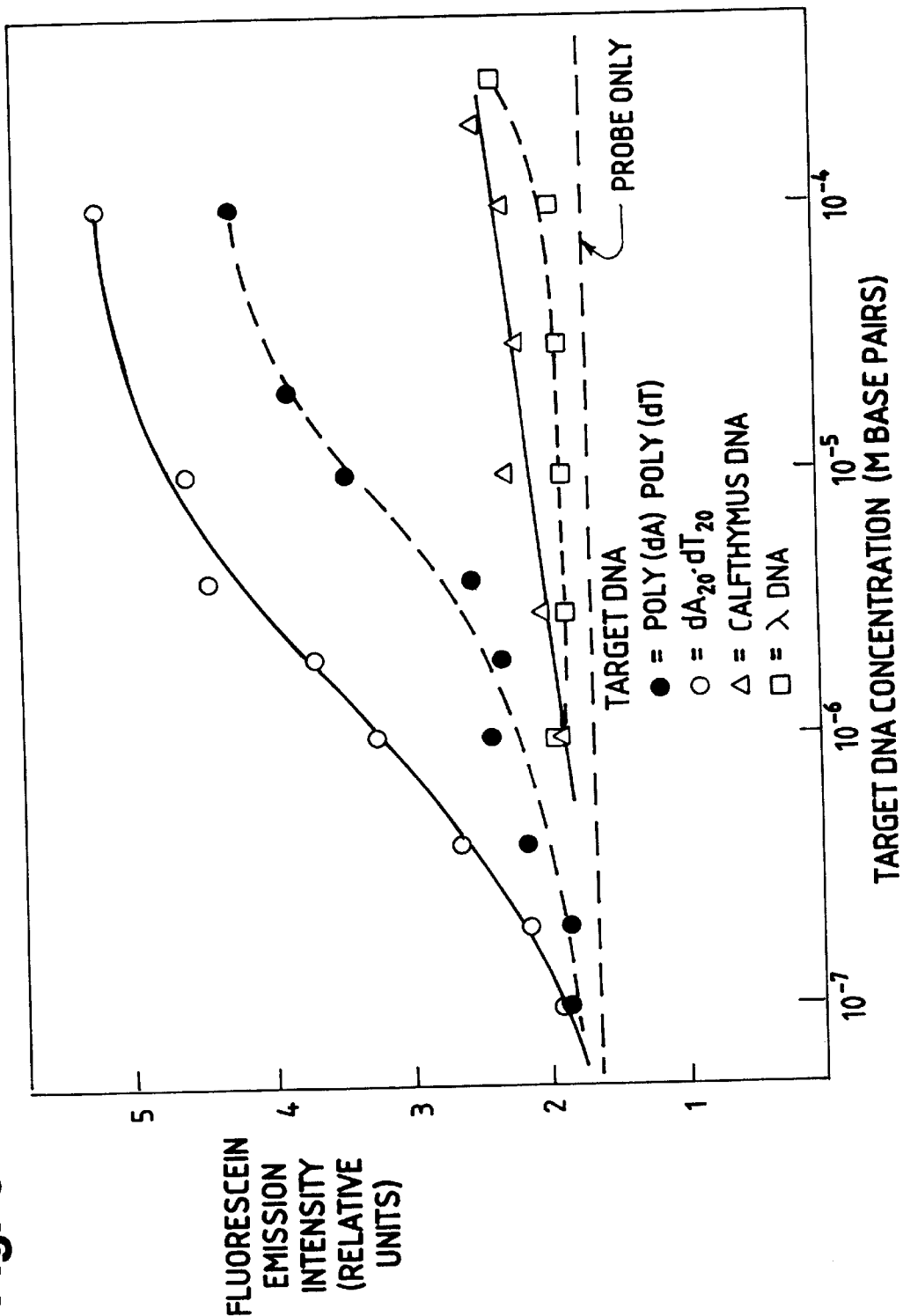
Figure 10:
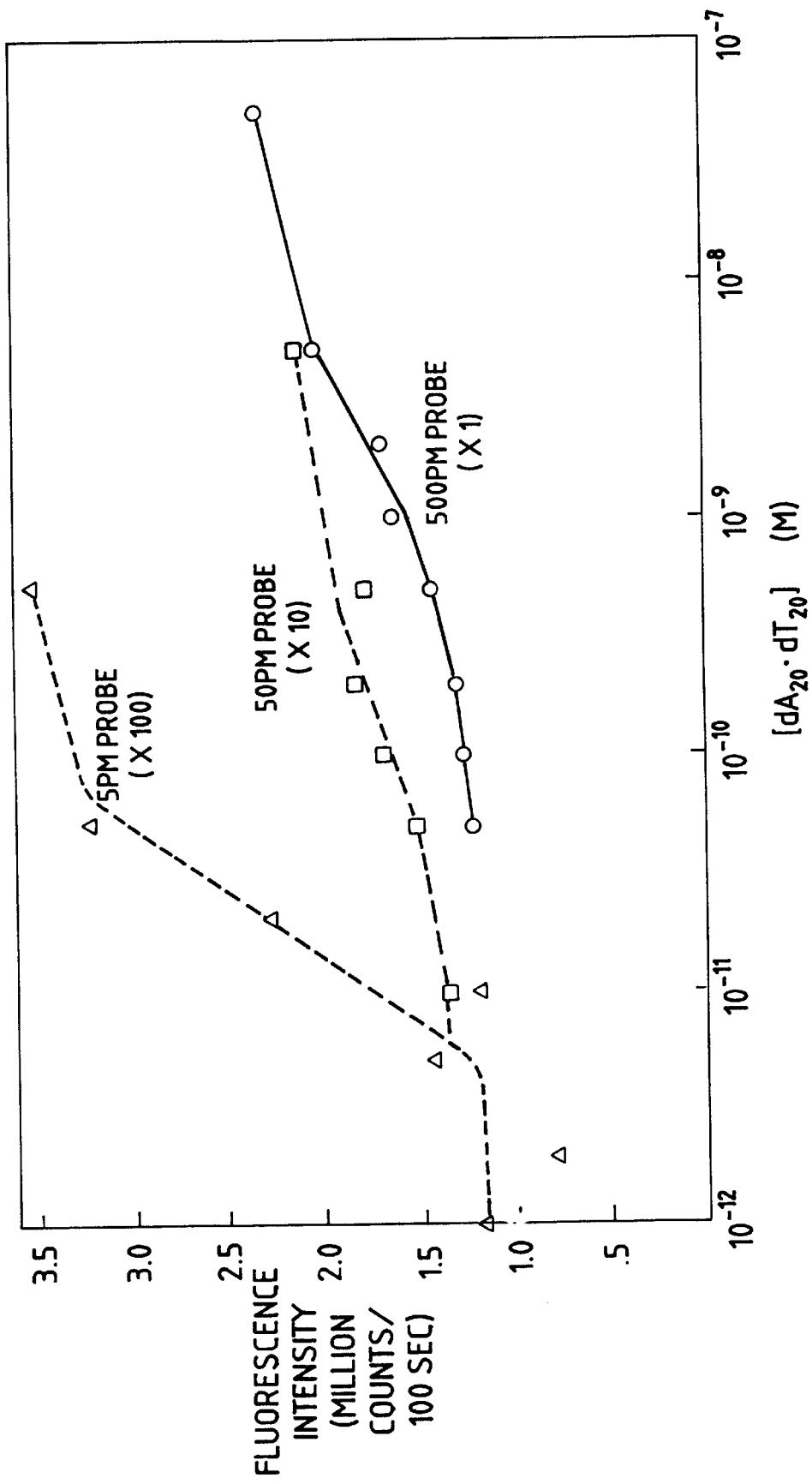

The fluorescence intensity data plotted in FIG. 9 shows the expected concentration dependent behavior for a competitive hybridization when the correct target DNA (dA$_{20}$:dT$_{20}$) was employed. Target DNA concentrations are plotted in terms of base pairs since different molecular weight targets were employed. The corresponding base pair concentration of labeled probe duplex included in each sample was 1 μM (50 nM duplex probe). The midpoint for fluorescence change occurred at about 1.2 μM dA$_{20}$:dT$_{20}$ which is close to the value of 1 μM expected for a competitive hybridization in which complementary target strands have the same affinity for each other as they do for complementary probe strands. The data collected using the noncomplementary target DNA (calf thymus and lambda DNA) show that the probe is specific for the dA$_{20}$:dT$_{20}$ target DNA since excess noncomplementary DNA does not prevent complementary probe strands from hybridizing to one another.

Hybridization assay sensitivity was demonstrated by performing competitive hybridizations at lower probe concentrations. Data obtained from competitive hybridizations using the labeled dA$_{20}$:dT$_{20}$ probe at 500 μM, 50 μM, and 5 μM concentrations is presented in FIG. 10. In these experiments probe was mixed with target DNA in buffer containing 100 mM NaCl and 10 mM potassium phosphate at pH 7.5. The samples were then heated to 80° C. for 10 minutes at which time the temperature was allowed to decrease to 20° C. at a rate of 5 degrees per hour. This was accomplished using a computer controlled water bath. Fluorescein emission was then measured for each sample at 20° C. The characteristic sigmoidal dependence of fluorescein emission intensity as a function of target concentration was observed at each probe concentration and the midpoint of the fluorescence intensity change occurred at lower target concentrations for assays using lower probe concentrations. For the assay series using the lowest probe concentration, 5 μM probe, the midpoint for fluorescence change was about 20 ∥M target. Samples used in these experiments were 1 ml in volume since standard semimicro fluorescence cuvettes were employed. This corresponds to 20 fmole of target DNA. DNA hybridizations by other techniques are often performed using volumes in the vicinity of 10 μl. Sample cells can be devised for fluorometers which permit similar volumes to be used and would therefore result in about a 100-fold increase in sensitivity to 200 amole for the midpoint of the fluorescence change. A large increase in sensitivity is not expected by reducing the probe concentration further since in the present experiment the maximum fluorescence change using 5 μM probe was approximately the same magnitude as the buffer fluorescence; in other words the signal-to-noise ratio was equal to one. Buffer background is subtracted from the data presented in FIG. 10.

One method which allows an increase in assay sensitivity is to employ multiple probes which hybridize to different regions of the genome(s) of interest. Two approaches to this were examined. In the first approach, multiple duplex probes were prepared from natural DNA by the use of restriction enzymes. The neomycin phosphotransferase gene was inserted into a pSP65 plasmid (Promega Biotech, Madison, Wisconsin) and the plasmid propagated in *Escherichia coli*. Several milligrams of the plasmid were then isolated from *E. coli* cultures and the plasmid DNA processed with two restriction enzymes, Alu I and Hae III. This produced approximately 37 blunt end duplexes per plasmid, ranging in size from about 6 base pairs to 600 base pairs (from DNA sequence analysis). The collection of duplexes was then labeled using the usual 5'- and 3'-labeling techniques as performed when labeling the dA$_{20}$:dT$_{20}$ probes. The neomycin phosphotransferase gene was not first isolated free from the pSP65 plasmid, as would generally be desired, in order to simplify this initial study. Several labeled preparations of this restriction cut plasmid are listed in Table 3.

Figure 11:
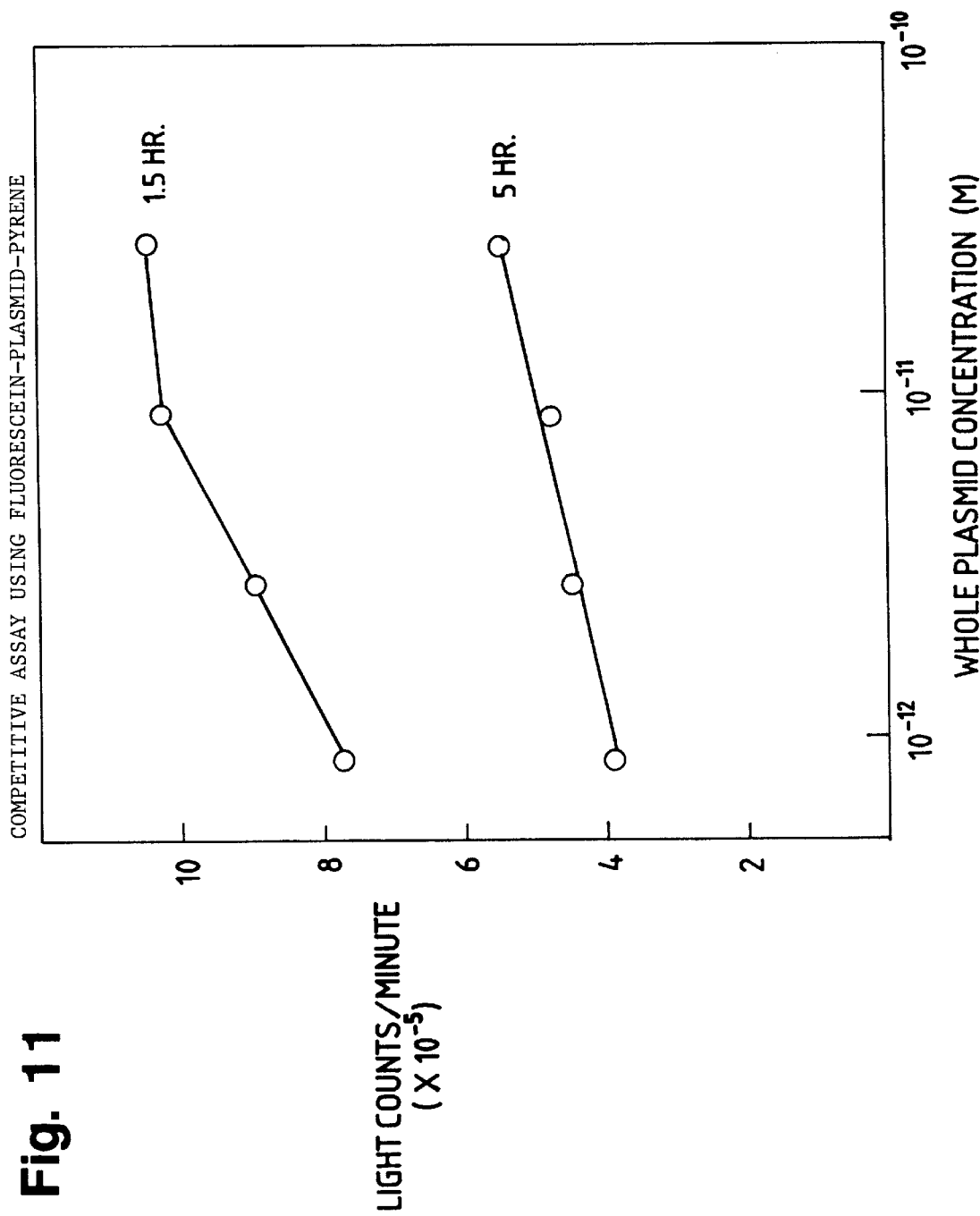

FIG. 11 presents data from a competitive hybridization performed using the first plasmid preparation listed in Table 3 to probe various concentrations of uncut pSP65 plasmid containing the neomycin phosphotransferase gene. The plasmid probe was present at a concentration which corresponded to 2.7 pM of whole plasmid (100 pM of total labeled duplexes). Probe and target DNA in water were placed in a boiling water bath for 12 minutes and then allowed to cool to room temperature with the addition of 2× concentrated binding buffer to bring the final NaCl and potassium phosphate concentrations to 1M and 10 mM, respectively.

Fluorescein emission was recorded at various times for each sample. Data plotted in FIG. 11 corresponds to fluorescence measured at 1.5 and 5 hours as indicated. Both sets of fluorescence values are shown to decrease with increasing target concentration as expected.

The target concentration range studied was not large enough to show the full range of fluorescence variation with temperature, however, the assay does display sensitivity to at least several picomoles which corresponds to the corresponding concentration of probe used in this assay. In a hypothetical 10 µl sample, several picomolar target corresponds to about 30 amole. Fluorescein emission intensity was more than an order of magnitude greater than background fluorescence in this experiment.

Hybridizations are expected to be difficult for a heterogeneous population of probes with regard to probe length and the consequential wide range of melting temperatures resulting from random restriction presentation of plasmids. It would be beneficial, therefore, to use careful selection of restriction enzymes to produce as homogeneous sized probe population as possible. New restriction sites may be engineered into the genome in order to produce such a homogeneous population from cloned DNA.

Figure 12:
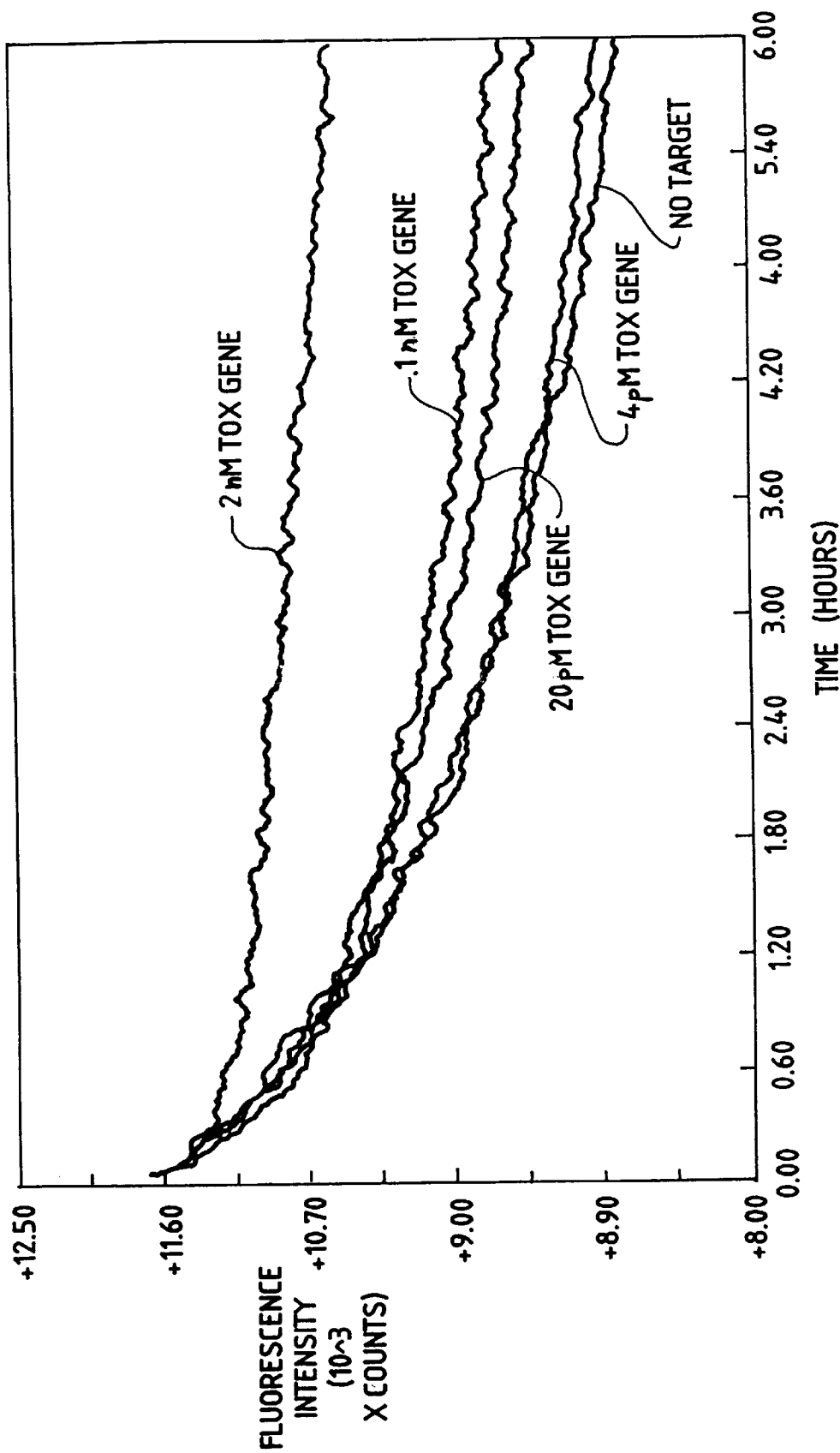

Turning now to FIG. 12, which sets forth an assay for *E. Coli* enterotoxin gene, target DNA, composed of the enterotoxin gene fragment of approximately 1000 base pair length, was mixed with 14 µg of lambda DNA (carrier DNA) in 700 µl of buffer containing 1 mM EDTA and 10 mM TRIS at pH 7.5. This solution was placed in a boiling water bath for 12 minutes after which time the duplex probe DNA, identified in Table 3 as "TOXIN," was added and the solution placed back in the boiling water bath for an additional 2 minutes. The solution was then added to 700 µl of 2× NaCl/phosphate buffer in a fluorescence cuvette contained within the thermostrated cuvette holder of the fluorometer and maintained at 42° C. (25 degrees below the probe melting temperature). The final sample concentrations of lambda DNA, sodium chloride, and potassium phosphate were 10 µg/ml, 1M, and 0.01M, respectively.

Fluorescence intensity was measured in a different manner than in previous experiments. The fluorescence values were recorded continuously with time by the use of a computer interfaced to the detector electronics (see Materials and Methods section). The data collected in this manner is plotted in FIG. 12 for samples containing various concentrations of enterotoxin target. By recording initial and final fluorescence values, a fluorescence change is obtained which is independent of background light levels which may be variable between samples. The data traces in FIG. 12 have been offset so that each set of data contains the same initial fluorescence values. The effect of this is to cancel out the background variation from sample to sample. The fluorescence change of each sample is related to the amount of target DNA present. The lowest target concentration detectable is shown to be 4 pM. A hypothetical 10 µl sample would, therefore, contain 40 amole of target at this concentration. A second advantage of recording the fluorescence intensity continuously with time is that shorter hybridization times may be used since the time dependence of the fluorescence changes may be fit by kinetic equations which would allow extrapolation of data to equilibrium values. The relative degree of fluorescence changes may be differentiated at times under two hours for the experiment shown in FIG. 12.

Although the foregoing examples recite individual fluorophores, the present invention would be applicable to other amine reactive fluorophores and chemiluminescent agents. Amine-reactive fluorophores include, by way of example, the aforementioned fluorescein, pyrene, acridine, sulforhodamine, eosin, erythrosin, and derivatives thereof. Amine-reactive chemiluminescent agents include, by way of example, microperoxidase, luminol, isoluminol, glucose oxidase, acridinium esters, and derivations thereof.

Chemiluminescent agents can be applied to the present assay in conjunction with a fluorophore in which the chemiluminescent label moiety of a probe would interact with a fluorophore of a second complementary probe. The fluorophore would quench the emissions of the chemiluminescent agent until the label moieties separate. Suitable chemiluminescent cofactors would be applied to the sample medium to initiate light-emitting reactions. As target competed for binding sites with probes, label moieties would be separated allowing the chemiluminescent agent or moiety to be unquenched and capable of generating a signal that could be detected.

A chemiluminescent agent could also be applied to the present invention in conjunction with chemiluminescent cofactors. Thus, a chemiluminescent label moiety of a first probe would interact with a chemiluminescent cofactor label moiety on a second complementary probe. The system would emit light of a particular intensity. Where target is present, target would compete with probes, thereby separating the first and second probes and the label moieties and reducing the light emission of the system.

Fluorophore labeled probes may be utilized in time resolved assay procedures to limit background fluoresence. Thus, a light pulse may be introduced at a wavelength sufficient to excite a first fluorophore. The first fluorophore transfers the energy to a second fluorophore. The transfer of energy from a first fluorophore to a second fluorophore and the emission of the energy by the second fluorophore is a slow process relative to direct fluorescence. The first fluorophore can be selected to have a long emission half-life to prolong the energy transfer process. The sample can be monitored for the light energy from the second fluorophore after the pulse, after direct fluorescent activity initiated by the pulse had terminated and during the interval in which transferred energy would be emitted by the second fluorophore. Only fluorescent groups in a position to transfer energy would produce emission which would be monitored. Only label moieties of complementary probes in a position to interact would have detectable signals thereby reducing background emission.

A further teaching of a time resolved assay procedure is set forth in my copending application Ser. No. 738,560, incorporated by reference herein.

Thus, the present invention features a homogeneous nonradioactive assay. Due to the homogeneous nature of the present assay, assays can be performed within shorter times. The use of nonradioactive labels allows the assays to be performed without special permits and simplifies assay techniques and manufacturing techniques.

Thus, while preferred embodiments have been illustrated and described, it is understood that the present invention is capable of variation and modification and, therefore, should not be limited to the precise details set forth, but should include such changes and alterations that fall within the purview of the following claims.

I claim:

1. A method for assaying a sample for target polynucleotides comprising:
   (a) contacting sample with reagent under binding conditions wherein said reagent includes a first polynucleotide probe and a second polynucleotide probe, said first and second probes capable of assuming a first position wherein said first and second probes are bound to each other and at least one of said probes capable of assuming a second position wherein said probe strand is bound to said target, said first probe and second probe including a first label moiety associated with one of said probes and including a second label moiety associated with said opposite probe, said first and second label moieties capable of interacting via energy transfer when said first and second probes are bound to each other to produce a signal capable of detection characteristic of the probe in one of said two positions, said first label moiety located at the 3'-terminus of one of said probes and said second label moiety located at the 5'-terminus of said other probe; and (b) monitoring said sample for said signal, the presence of which is related to the presence of target in said sample.

2. The method of claim 1 wherein each probe has a plurality of label moieties.

3. The method of claim 2 wherein each such label moiety is located at the termini of said probes.

4. The method of claim 2 wherein said first label moiety is located at the 3'-terminus of one of said probes and said second label moiety is located at the 5'-terminus of said opposite probe.

5. The method of claim 4 wherein said label moiety at the 3' terminus is a fluorescent derivative of a nucleotide.

6. The method of claim 5 wherein the label moiety is 1-$N^6$-ethenoadenosine-5'-monophosphate.

7. The method of claim 1 wherein said first label moiety is associated to said probe by an aminoalkyl derivative of the terminal nucleotide.

8. The method of claim 7 wherein said derivative is an aminoalkyl derivative of adenine.

9. The method of claim 7 wherein said derivative is an aminohexyl derivative of adenine.

10. The method of claim 7 wherein said derivative is 8-(6-aminohexyl)-aminoadenosine-5'-monophosphate.

11. The method of claim 1 further comprising the additional steps of: splicing polynucleotide segments having base sequences substantially identical to said target sequence into amplification means to form multiple copies of said polynucleotide segments, isolating said segments, and associating said first and second label moieties to the termini of said segments to form probes.

12. The method of claim 11 wherein amplication means include plasmids and phage particles.

13. The method of claim 11 wherein said segments, after isolation, are subjected to restriction digestion to form further subsegments, and said subsections are associated with said label moieties to form probes.

14. A kit for assaying a sample for target polynucleotides comprising reagent, wherein said reagent includes a first polynucleotide probe and a second polynucleotide probe, said first and second probes capable of assuming a first position wherein said first and second probe are bound to each other and at least one of said probes capable of assuming a second position wherein said probe strand is bound to said target, said first probe and second probe including a first label moiety associated with one of said probes and including a second label moiety associated with said opposite probe, said first and second label moieties capable of interacting via energy transfer when said first and second probes are bound to each other to produce a signal capable of detection which is characteristic of the probe in one of said two positions, said first label moiety located at the 3'-terminus of one of said probes and said second label moiety located at the 5'-terminus of said other probe.

15. The kit of claim 14 wherein each probe has a plurality of label moieties.

16. The kit of claim 15 wherein each such label moiety is located at the termini of said probes.

17. The kit of claim 15 wherein said first label moiety is located at the 3'-terminus and said second label moiety is located at the 5'-terminus.

18. A method for assaying a sample for target nucleic acid comprising;

(a) contacting sample with reagent under binding conditions wherein said reagent includes a first nucleic acid probe and a second nucleic acid probe, said first and second probes capable of assuming a first position wherein said first and second probe are bound to each other and at least one of said probes capable of assuming a second position wherein said probe strand is bound to said target, said first probe and second probe including a first fluorophore label moiety associated with one of said probes and including a second fluorophore label moiety associated with said opposite probe, said first and second label moieties capable of interacting via energy transfer when said first and second probes are bound to each other to produce a signal capable of detection characteristic of the probe in one of said two positions, said first label moiety located at the 3'-terminus of one of said probes and said second label moiety located at the 5'-terminus of said other probe; and (b) monitoring said sample for said signal, the presence of which is related to the presence of target in said sample.

* * * * *